(12) United States Patent
Xu et al.

(10) Patent No.: US 6,368,855 B1
(45) Date of Patent: Apr. 9, 2002

(54) MHC CLASS II ANTIGEN PRESENTING CELLS CONTAINING OLIGONUCLEOTIDES WHICH INHIBIT Ii PROTEIN EXPRESSION

(75) Inventors: Minzhen Xu, Northborough; Gang Qiu, Shewsbury; Robert Humphreys, Acton, all of MA (US)

(73) Assignee: Antigen Express, Inc., Worcester, MA (US)

( * ) Notice: Subject to any disclaimer, the term of this patent is extended or adjusted under 35 U.S.C. 154(b) by 0 days.

(21) Appl. No.: 09/205,995

(22) Filed: Dec. 4, 1998

Related U.S. Application Data

(63) Continuation-in-part of application No. 09/036,746, filed on Mar. 9, 1998, now abandoned, which is a continuation of application No. 08/661,627, filed on Jun. 11, 1996, now Pat. No. 5,726,020.

(51) Int. Cl.$^7$ .................................................. C12N 5/08
(52) U.S. Cl. ........................................ 435/366; 435/325
(58) Field of Search ..................... 435/6, 325; 536/23.5

(56) References Cited

U.S. PATENT DOCUMENTS

| | | | |
|---|---|---|---|
| 5,726,020 A | 3/1998 | Humphreys et al. ........... | 435/6 |
| 5,858,776 A | * 1/1999 | Ostrand-Rosenberg et al. .. | 435/325 |

OTHER PUBLICATIONS

Strubin et al. EMBO J. (Apr. 1984) 3(4) :869–872.*
Clements et al., *J. of Immunol. 149*: 2391–2396 (1992).
Baskar et al., *Cell. Immunol. 155*: 123–133 (1994).
Baskar et al., *J. Exp. Med. 181*: 619–629 (1995).
Armstrong et al., *Proc. Natl. Acad. Sci. USA 94*: 6886–6891 (1997).
Chen and Ananthaswamy, *J. of Immunol. 151*: 244–255 (1993).
Moudgil et al., *J. Immunol. 159*: 2574–2579 (1997).
Bertolino et al., *Crit. Reviews in Immunol. 16*: 359–379 (1996).
Bertolino et al., *International Immunology 3*: 435–443 (1991).
Ostrand–Rosenberg et al., *J. of Immunol. 144*: 4068–4071 (1990).

* cited by examiner

*Primary Examiner*—Lisa B. Arthur
(74) *Attorney, Agent, or Firm*—Kevin M. Farrell

(57) ABSTRACT

Disclosed is a specific regulator of Ii protein expression or immunoregulatory function. Specifically disclosed are several forms of the specific regulator of Ii, including those which function through the formation of a duplex molecule with an RNA molecule encoding mammalian Ii protein to inhibit Ii protein synthesis at the translation level. This class includes copolymers comprised of nucleotide bases which hybridize specifically to the RNA molecule encoding mammalian Ii protein, and also expressible reverse gene constructs. In other aspects, the disclosure relates to MHC class II-positive antigen presenting cells containing a specific regulator of Ii expression. Such cells are useful, for example, in the display of autodeterminant peptides in association with MHC class II proteins. Compositions of the invention find application in methods for treating diseases, for example malignancies and autoimmune disorders, in a patient by enhancing immunological attack on undesired cells. An additional application is the isolation of autodeterminant peptides from a cell.

39 Claims, No Drawings

MHC CLASS II ANTIGEN PRESENTING CELLS CONTAINING OLIGONUCLEOTIDES WHICH INHIBIT Ii PROTEIN EXPRESSION

RELATED APPLICATIONS

This application is a continuation-in-part of U.S. application Ser. No. 09/036,746 abandoned, which is a continuation of U.S. application Ser. No. 08/661,627 (now U.S. Pat. No. 5,726,020).

BACKGROUND OF THE INVENTION

The immune response to specific antigens is regulated by the recognition of peptide fragments of those antigens by T lymphocytes. Within an antigen presenting cell, peptide fragments of the processed antigen become bound into the antigenic peptide binding site of major histocompatibility complex (MHC) molecules. These peptide-MHC complexes are then transported to the cell surface for recognition (of both the foreign peptide and the adjacent surface of the presenting MHC molecule) by T cell receptors on helper or cytotoxic T lymphocytes. There are two classes of MHC molecules that deliver peptides, MHC class I and MHC class II.

MHC class I molecules present antigen to CD8-positive cytotoxic T-lymphocytes, which then become activated and can kill the antigen presenting cell directly. Class I MHC molecules exclusively receive peptides from endogenously synthesized proteins, such as an infectious virus, in the endoplasmic reticulum at around the time of their synthesis.

MHC class II molecules present antigen to CD4-positive helper T-lymphocytes (T helper cells). Once activated, T helper cells contribute to the activation of cytotoxic T lymphocytes (T killer cells) and B lymphocytes via physical contact and cytokine release. Unlike MHC class I molecules, MHC class II molecules bind exogenous antigens which have been internalized via non-specific or specific endocytosis. Around the time of synthesis MHC class II molecules are blocked from binding endogenous antigen by instead binding the invariant chain protein (Ii). These MHC class II-Ii protein complexes are transported from the endoplasmic reticulum to a post-Golgi compartment where Ii is released by proteolysis and exogenous antigenic peptides are bound (Daibata et al., *Molecular Immunology* 31: 255–260 (1994); Xu et al., *Molecular Immunology* 31: 723–731 (1994)).

MHC class I and MHC class II molecules have a distinct distribution among cells. Almost all nucleated cells express MHC class I molecules, although the level of expression varies between cell types. Cells of the immune system express abundant MHC class I on their surfaces, while liver cells express relatively low levels. Non-nucleated cells express little or no MHC class I. MHC Class II molecules are highly expressed on B lymphocytes and macrophages, but not on other tissue cells. However, many other cell types can be induced to express MHC class II molecules by exposure to cytokines.

Under normal conditions, endogenous peptides (with self determinants potentially leading to autoimmune disease) are not bound to MHC class II molecules since the Ii protein is always cosynthesized with nascent MHC class II molecules. Because complexes containing autodeterminant peptides and MHC class II molecules are never seen by the body's immune surveillance system, tolerance is not developed to these determinants. If MHC class II molecules are not inhibited by Ii in a developed individual, endogenous autodeterminants then become presented by MHC class II molecules, initiating an autoimmune response to those endogenous antigens. Such is the case in certain autoimmune diseases. By engineering such an effect in malignant cells, an "autoimmune response" to the endogenous antigens of a tumor can be used therapeutically to either restrict growth or eliminate tumor cells.

The therapeutic effects of increased MHC class II molecule expression without concomitant increase in Ii protein has been demonstrated in MHC class II-negative, Ii-negative tumors (Ostrand-Rosenberg et al., *Journal of Immunol.* 144: 4068–4071 (1990); Clements et al., *Journal of Immunol.* 149: 2391–2396 (1992); Baskar et al., *Cell. Immunol.* 155: 123–133 (1994); Baskar et al., *J. Exp. Med.* 181: 619–629 (1995); and Armstrong et al., *Proc. Natl. Acad. Sci. USA* 94: 6886–6891 (1997)). In these studies, transfection of genes for MHC class II molecules into a MHC class II-negative murine sarcoma generated MHC class II-positive, but Ii-negative tumor cell lines. Injection of these cells into a MHC compatible host led to the delayed growth of the parental tumors. Co-transfection of the gene for the Ii protein into a sarcoma cell line along with the MHC class II genes, inhibited the tumor-therapeutic effect of the MHC class II genes since the Ii chain blocked the presentation of endogenous tumor antigens. Comparable results have been produced with a murine melanoma (Chen and Ananthaswamy, *Journal of Immunology* 151: 244–255 (1993)).

The success of this therapeutic approach is thought to involve the natural activities of dendritic cells. Dendritic cells are professional scavengers, which process foreign antigens into peptides and present them to T lymphocytes from MHC antigens on their cell surfaces. Dendritic cells have the capacity to present antigen through both MHC class I and class II molecules, enabling them to activate both T helper and T killer cells. It is thought that an effective T helper cell response is required to elicit a powerful T killer cell response and that the combined activation produced by dendritic cells leads to a heightened anti-tumor response (Ridge et al., *Nature* 193: 474–477 (1998); Schoenberger et al., *Nature* 193: 480–483 (1998)). The dendritic cells of macrophage lineage, upon finding tumor cells, ingest and process both tumor-specific and tumor-related antigens. The dendritic cells then migrate to the lymph nodes which drain the tumor site and reside in those nodes near the node cortex where new T cells germinate. In the node cortex, resting T killer cells which recognize tumor determinants on the dendritic cells, become activated and proliferate, and are subsequently released into the circulation as competent, anti-tumor, killer T cells.

Although interaction with T-helper cells activates or "licenses" dendritic cells to present antigen through MHC class I molecules, and hence to activate T killer cells, simultaneous interaction with T helper cells and T killer cells is not necessary; activated dendritic cells maintain their capacity to stimulate T killer cells for some time after T helper cell mediated activation. The respective antigenic peptides which become presented by either MHC class II or MHC class I determinants do not need to come from one antigenic protein, two or more antigens from a malignant cell can be processed and presented by a dendritic cell. Therefore, licensing to one determinant, perhaps not tumor specific, carries with it the power to license activation of T killer cells to other, perhaps tumor-specific, determinants. Such 'minor' or 'cryptic' determinants have been used for various therapeutic purposes (Mougdil et al., *J. Immunol.* 159: 2574–2579 (1997)).

Experimental alteration of MHC class II antigen presentation is thought to expand immune responses to these minor determinants. The series of peptides usually unavailable for charging to MHC class II molecules, provides a rich source of varied peptides for MHC class II presentation. Exploitation of this series of determinants leads to the expansion of populations of responsive T helper cells. Such expanded populations can elicit dendritic cell licensing, some of which are directed toward tumor specific and tumor related determinants. Although normal cells potentially share tumor cell determinants, only minor cellular damage occurs to normal cells. This is because the multiple effector responses (mass of killer T cells, ambient activating cytokines, phagocytosing macrophages and their products, etc.) of the anti-tumor response is not directed towards normal cells.

Normal MHC class II antigen presentation can be altered by inhibiting the interactions of MHC class II molecules with the Ii protein. This is accomplished by decreasing total Ii protein, (e.g. by decreasing expression) or by otherwise interfering with the Ii immunoregulatory function. Inhibition of Ii expression has been accomplished using various antisense technologies. An antisense oligonucleotide interacting with the AUG site of the mRNA for Ii protein has been described to decrease MHC class II presentation of exogenous antigen (Bertolino et al., *Internat. Immunology* 3: 435–443 (1991)). However, the effect on the expression of Ii protein and on the presentation of endogenous antigen by MHC class II molecules were not examined. More recently, Humphreys et al., U.S. Pat. No. 5,726,020 (1998) have identified three antisense oligonucleotides and a reverse gene construct which upon introduction into an antigen presenting cell expressing MHC class II molecules expressing effectively suppresses Ii protein expression. Mice inoculated with tumor cells which are Ii suppressed by this mechanism were shown to survive significantly longer than mice inoculated with the untreated parent tumor cells. This observation indicates that the suppression of Ii protein generated an increase in range of antigenic determinant presentation, triggering a more effective immune response to the tumor cells.

SUMMARY OF THE INVENTION

In one aspect the present invention relates to a specific regulator of Ii protein expression or immunoregulatory function. Specifically disclosed are several forms of the specific regulator of Ii, including those which function through the formation of a duplex molecule with an RNA molecule encoding mammalian Ii protein to inhibit Ii protein synthesis at the translation level. This class includes copolymers comprised of nucleotide bases which hybridize specifically to the RNA molecule encoding mammalian Ii protein, for example antisense oligonucleotides, and also expressible reverse gene constructs which encode RNA molecules which hybridize specifically to the Ii RNA. In other aspects, the disclosure relates to MHC class II-positive antigen presenting cells containing a specific regulator of Ii expression. Such cells are useful, for example, in the display of autodeterminant peptides in association with MHC class II proteins. In another embodiment, the invention relates to methods for treating diseases, for example malignancies and autoimmune disorders, in a patient by enhancing immunological attack on the undesired cells. These methods involve providing an MHC class II-positive antigen presenting cell and introducing a specific regulator of Ii protein expression to enhance presentation of endogenous antigenic determinants. These cells or products thereof are then used to stimulate the immune system of the patient.

DETAILED DESCRIPTION OF THE INVENTION

A combination of previous discoveries collectively indicate that inhibition of Ii protein expression in a MHC class II antigen presenting cell abrogates the function of Ii protein and profoundly alters the range and selection of antigenic epitopes that are presented by MHC class II molecules to the immune system. It has previously been shown that Ii protein expression in cells can be inhibited specifically and efficiently with antisense technology using specific oligonucleotides or reverse gene constructs. U.S. Pat. No. 5,726,020 (Humphreys et al.) exemplifies this previous work and the disclosure of this patent is incorporated herein by reference. The present invention is based in part on the discovery of additional compositions which produce inhibition of Ii protein expression. These compositions and the methods with which they were identified are disclosed herein. Arising from these discoveries is the discovery that the enhanced presentation of antigenic determinants which results from blocking Ii protein expression or immunomodulatory function of a cell within an individual leads to an immune response which clears a related cell population from the individual. This discovery is utilized in the present invention to effect several useful therapeutic goals, many of which are directed towards clearing an undesired cell population from an individual.

One aspect of the present invention is a specific regulator of Ii protein expression or immunoregulatory function (the oligonucleotide CTCGGTACCTACTGG (SEQ ID NO:1) being specifically excluded). Delivery of this specific regulator of Ii to a cell which expresses MHC class II molecules alters the range and selection of antigenic determinants to which the MHC class II molecules of the cell bind, thus altering the antigen presentation of that cell. Several compositions function as specific regulators of Ii and each can be classified by their mechanism of action.

In one embodiment, the specific regulator of Ii functions through the formation of a duplex molecule with an RNA molecule encoding mammalian Ii protein. The formation of the duplex molecule inhibits Ii protein synthesis at the translation level. This specific regulator may contain nucleotide bases appropriately spaced on a copolymer backbone in a manner to effect binding of the nucleotide bases with other bases of the Ii RNA by Watson-Crick base pairing. Ii RNA sequences which are involved in the formation of the duplex molecule can be without limitation in: protein coding segments (exons), in the intervening segments (introns), overlapping between exons and introns (splice sites), at the initiation site for protein translation (AUG sites), upstream to the AUG site (for example at CAP sites, or other sequence-specific regulatory sites), or downstream from the coding segments (in 3' polyadenylation sequence-specific regulatory sites).

Two generic types of specific regulators can be used to form the duplex molecules with the Ii RNA. In the first type, chemically synthesized copolymers containing 10 to 50 nucleotide bases have been used. These copolymers contain nucleotide base sequences which are complementary to a targeted portion of the RNA molecule, otherwise known as antisense sequences. One example of such a copolymer is an antisense oligonucleotide. Copolymers inhibit protein translation from RNA by two mechanisms. One method is to block access to portions of the RNA which must interact with ribosomes, spliceosomes or other factors essential for RNA maturation or translation. A second method, involves potentiation of an enzyme, ribonuclease H, which cleaves sequences of RNA hybridized to DNA. Thus, the binding of a DNA or DNA like copolymer to a corresponding segment in the RNA leads to cleavage of the RNA at the copolymer binding site.

Copolymers hybridize to the target RNA by Watson-Crick base pairing. The sequence of an copolymer is defined by the complementary sequence of the target RNA. The copolymers are usually synthesized chemically with nucleotide sequence lengths which span at least 6 complementary nucleotides of the target RNA, with 12–25 being most common. Statistically, a sequence of about 15 nucleotides is unique within the population of all RNAs within a cell, enabling any particular RNA to be targeted with a high degree of specificity. Binding to RNA is also very stable with Kd values around $10^{-17}$ M, for a copolymer encompassing 20 base pairs.

In some cases, cells in culture spontaneously take up copolymers in a sufficient amount to achieve a useful effect. Such uptake appears to be an active process requiring biochemical energy and participation of certain cell surface proteins. Uptake can also occur by pinocytosis. This route can be enhanced by incubating cells in a hypertonic medium containing a copolymer followed by resuspension of the cells in a slightly hypotonic medium to induce bursting of intracellular pinocytotic vesicles. In other cases, uptake can be assisted by use of lipids or liposomes, by electroporation, or by streptolysin O treatment to permeabilize the cell membrane. Cells in vivo often take up copolymers more readily than do cultured cells. Optimal conditions for cell uptake of copolymers by electroporation are revealed in Example 2 below.

Potential sites of the target RNA are those open for binding of functional complexes of proteins, and additional sites which are otherwise open for copolymer binding. Such sites can be identified using ribonuclease H (RNase H), an enzyme which cleaves RNA that is hybridized to DNA. By adding DNA oligonucleotides, singly or in mixtures, to 5'-radiophosphorus-labeled RNA in the presence of ribonuclease H, the sites on the RNA where oligonucleotides and other copolymers hybridize are identified after gel electrophoresis of the RNA and autoradiography. Such experiments with Ii antisense oligonucleotides are presented in Example 1. The sites in the Ii RNA found in the present invention to be most open for RNase H cleavage, were the region of the AUG initiator codon and the region of the first splice site in the pre-mRNA.

The term "oligonucleotide" regarding the present invention refers to polynucleotides comprising nucleotide units formed with naturally occurring bases and pentofuranosyl sugars joined by phosphodiester linkages. The term "copolymer" includes oligonucleotides and also structurally related molecules formed from non-naturally occurring or modified subunits of oligonucleotides. These modifications occur either on the base portion of a nucleotide, on the sugar portion of a nucleotide, or on the internucleotide linkage groups. Additional linkage groups are often also substituted for sugar and phosphate backbone of a natural oligonucleotide to generate a copolymer, discussed in greater detail below.

Such oligonucleotide modifications and the characteristics which are produced are readily available to one of skill in the art. Exemplary modifications are presented in U.S. Pat. No. 4,469,863 (1984); U.S. Pat. No. 5,216,141 (1993); U.S. Pat. No. 5,264,564 (1993); U.S. Pat. No. 5,514,786 (1996); U.S. Pat. No. 5,587,300 (1996); U.S. Pat. No. 5,587,469 (1996); U.S. Pat. No. 5,602,240 (1997); U.S. Pat. No. 5,610,289 (1997); U.S. Pat. No. 5,614,617 (1997); U.S. Pat. No. 5,623,065 (1997); U.S. Pat. No. 5,623,070 (1997); U.S. Pat. No. 5,700,922 (1997); and U.S. Pat. No. 5,726,297 (1998), the disclosures of which are incorporated herein by reference.

The ability of oligonucleotides to hybridize to complementary RNA is very tolerant of chemical modifications. Therefore, many different functional copolymers are possible. The sugar phosphate backbone, in particular, can be altered extensively without losing the ability to form Watson-Crick base pairs. By definition, a nucleotide comprises a sugar, nitrogen heterocycle and phosphate moieties. Some synthetic analogues of oligonucleotides lack either a sugar or phosphate group or both yet still can hybridize by Watson-Crick base pairs in the same way as antisense oligonucleotides and can be used for the same purposes. These copolymers containing nucleotide bases are functional equivalents of oligonucleotides in hybridizing to RNA. Summarized below are some of the modifications to oligonucleotides which change and improve their properties for antisense applications.

1. One of the non-bridging oxygen atoms of the phosphate is replaced by sulfur (Agrawal et al., *Proc. Natl. Acad. Sci. USA* 85: 7079–7083 (1988)), selenium (Mori et al., *Nucleic Acids Res.* 17: 8207–8219 (1989)) or substituted boron (Porter et al., *Nucleic Acids Res.* 25: 1611–1617 (1997)) to give negatively charged analogues.
2. Both non-bridging oxygen atoms are replaced with sulfur (Vaughn et al., *Nucleic Acids Res.* 24: 4558–4564 (1996)).
3. One of the non-bridging oxygen atoms are esterified or replaced by a methyl or substituted nitrogen atom to give uncharged phosphotriesters (Hayakawa et al., *J. Org. Chem.* 60: 925–930 (1995); Iyer et al., *Tetrahedron* 52: 14419–14436 (1996); Zhang et al., *Bioorg. Medicinal. Chem. Letter* 6: 1911–1916 (1996)), phosphonates (Sarin et al., *Proceedings of the National Academy of Science USA* 85: 7448–7451 (1988)) or phosphoramidates (Agrawal et al., *Proc. Natl. Acad. Sci. USA* 85: 7079–7083 (1988)).
4. The two bridging oxygen atoms are replaced by sulfur or nitrogen in different permutations and combinations (Gryaznov et al., *Nucleic Acids Res.* 24: 1508–1514 (1996); Goodchild, *Bioconjugate Chem.* 1: 165–187 (1990)).
5. The above substitutions are combined (e.g. to produce methylphosphonothioate) (Padmapriya & Agrawal, *Bioorganic & Medicinal Chemistry Letters* 3: 761–764 (1993)).
6. The internucleoside phosphate group are replaced by other arrangements of atoms that do not contain phosphorus and are uncharged (Sanghvi & Cook, Carbohydrates: synthetic methods and applications in antisense therapeutics. An overview. Chap. 1. In: *Carbohydrate Modifications in Antisense Research.* (:Sanghvi, Cook) (ACS Symposium Series, 580). American Chemical Society, Washington, D.C. 1–22 (1995); De Mesmaeker et al., *Account. Chem. Res.* 28: 366–374 (1995); Kiely, *Nucleic Acids Res.* 20: 1339–1344 (1994)).
7. The sugar is ribose or 2'-deoxyribose. The 2'-hydroxyl group in ribose is alkylated or replaced by halogen, amino, or carbon substituents (Kiely, *Nucleic Acids Res.* 20: 1339–1344 (1994); De Mesmaeker et al., *Account. Chem. Res.* 28: 366–374 (1995); Sanghvi & Cook, Carbohydrates: synthetic methods and applications in antisense therapeutics. An overview. Chap. 1. In: *Carbohydrate Modifications in Anti sense Research.* (:Sanghvi, Cook) (ACS Symposium Series, 580). American Chemical Society, Washington, D.C. 1–22 (1995); Freier & Altmann, *Nucleic Acids Res.* 25: 4429–4443 (1997)) or mercapto (Hamm & Piccirilli, *J. Org. Chem.* 62: 3415–3420 (1997)).
8. Stereochemistry around the sugar ring is changed at the 1' position to give the α-nucleoside series (Lavignon et al., *Antisense Research and Development* 2: 315–324

(1992)), at the 2'-position to give the arabinose series, or at the 3'-position to give the xylose series (Seela et al., *Helv. Chim. Acta.* 79: 1451–1461 (1996)).
9. Sugars are furanosyl or pyranosyl (Pitsch et al., *Helv. Chim. Acta.* 78: 1621–1635 (1995)), pentoses or hexoses (Herdewijn, *Liebigs Annalen* 1996: 1337–1348 (1996)).
10. Ribofuranosyl rings are made more rigid to improve hybridization by fusing a second ring across the C3'–C5' positions or between the sugar and base (Tarkoy et al., *Helv. Chim. Acta.* 77: 716–744 (1994); Herdewijn, *Liebigs Annalen* 1996: 1337–1348 (1996)).
11. The nucleotides are linked 3'–5' (as normal) or 2'–5' (Maran et al., *Science* 265: 789–792 (1994)).
12. The sugar is replaced by morpholine (Summerton et al., *Antisense Nucleic Acid Drug D.* 7: 63–70 (1997)).
13. The sugar phosphate backbone is replaced by a peptide backbone to give a "peptide nucleic acid" (pna) (Egholm et al., *Nature* 365: 566–568 (1993)).

Currently, the following subset of modifications are used most commonly:

The sugar is 2'-deoxyribose or 2'-o-methyl ribose [or 2'-O-allyl ribose or 2'-O-(2-methoxy)ethyl ribose] and the phosphate group is one of the following:
1. unmodified phosphodiester
2. with a non-bridging oxygen replaced by sulfur (phosphorothioate), methyl (methylphosphonate) or substituted nitrogen (phosphoramidate)
3. with the oxygen atom bridging to C3' replaced by NH (phosphoramidate).

Among the oligonucleotide equivalents, the peptide nucleic acids and the morpholino derivatives are used most commonly as effective copolymers. Pyrrole-imdazole polyamides can also be employed (Gottesfeld, J. M., *Nature* 387: 202–205 (1997)).

Each modification has different properties and various modifications can be combined in a single oligonucleotide chain to produce a copolymer with the desired properties. For example, a central block of phosphodiester or phosphorothioate linkages that activate ribonuclease H can be combined with flanking sequences that are more resistant to exonucleases (U.S. Pat. No. 5,491,133 (1996)).

Bases of the copolymer can be modified providing that this does not interfere with Watson-Crick base pairing. Such modifications are commonly utilized to increase hybrid stability. Examples are 5-substituted cytosine or uracil, especially 5-propynyl cytosine and 5-propynyl uracil, to replace C or U and T respectively, or 2,6-diaminopurine to replace A (Freier & Altmann, *Nucleic Acids Res.* 25: 4429–4443 (1997)).

Due to secondary and tertiary structure of mRNA, some parts of the molecule may be inaccessible or unavailable for copolymer hybridization. RNA sites which are available to protein binding are more likely accessible for copolymer binding. These include the 5'-cap and AUG initiator codon where ribosome assembly occurs, splice sites in pre-mRNA and the polyadenylation signal (Goodchild et al., *Proceedings of the National Academy of Science USA* 85: 5507–5511 (1988); Dominski & Kole, *Mol. Cell. Biol.* 14: 7445–7454 (1994)). In cell-free studies of translation, it was found that the 5'-cap of a mRNA and the AUG initiator codons were particularly effective sites and that an oligonucleotide hybridized to the cap hindered binding of the ribosome and assembly of polysomes (Goodchild et al., *Arch. Biochem. Biophys.* 263: 401–409 (1988)).

In initial studies, detailed in Examples 1 and 3 of the Exemplification section which follows, the copolymers listed in SEQ ID NO: 40 (Table 1) which is complementary to the AUG initiator region, and in SEQ ID NO: 32, which is complementary to the first splice donor site in the Ii mRNA, demonstrated the greatest activity at hybridization and Ii inhibition.

Upon identification of the regions available for copolymer binding, additional overlapping copolymers were synthesized to find the most active sequence with which to target these regions (Table 5). These copolymers were assayed as before and examined for activity in Ii inhibition (Table 6A) as well as for cytotoxicity (Table 6B). The most active compound by these criteria, SEQ ID NO: 54, is complementary to the AUG initiator and also produces minimal effects on MHC class II expression, recovery and viability of the cells. The copolymer listed in SEQ ID NO: 62, corresponding to sequence which is complementary to a portion of exons bounding a splice site of the RNA molecule, more specifically to sequences in the first splice donor region, also demonstrates strong activity.

As presented in the Exemplification section which follows, specific copolymers hybridize to specific segments of Ii RNA, as revealed with the RNase H assay, and suppress Ii protein expression, as revealed with the immunofluorescence FACS assay. Among the copolymers complementary to the translation initiation site, SEQ ID NO: 54, SEQ ID NO: 53, SEQ ID NO: 52, SEQ ID NO: 40, SEQ ID NO: 55 are effective in the RNase H assay and are particularly active in suppression of Ii expression. The copolymers complementary to a portion of exons bounding a splice site, SEQ ID NO: 32 and SEQ ID NO: 62, are effective in the RNase H assay and also active in suppression of Ii expression. Additional copolymers which bind to regions within the exon and intron boundaries of a splice site inhibit intron splicing, and therefore Ii protein expression. Specifically the oligonucleotide which is complementary to a portion of the 3' end of the first exon and a portion of the 5' end of the first intron inhibit intron splicing, and therefore Ii protein expression. Among the oligonucleotides which are complementary to a region 3' of the termination codon, SEQ ID NO: 64, for example, inhibits Ii protein expression. Among the oligonucleotides which are complementary to a region 5' of the initiation codon, SEQ ID NO: 48, for example, inhibits Ii protein expression. Among the oligonucleotides which are complementary to a region encoding the CLIP peptides, SEQ ID NO: 11, for example, inhibits Ii protein expression.

In addition to backbone modifications described above, other groups can be conjugated to sites on the copolymer to enhance its activity in various ways. These groups are divided into functional categories. Chemical groups such as alkylating agents and other active species are conjugated at terminal or internal sites of the copolymer to cross-link the copolymer to the hybridized RNA molecule. Other chemical groups are so conjugated to catalyze cleavage of the hybridized RNA molecule (e.g. chelating agents). Ribozymes engineered into the copolymer also promote the cleavage of the Ii RNA. Another category of chemical groups that is conjugated to the copolymer intercalates into the nucleotide bases of the RNA molecule to stabilize hybridization of the copolymer and the Ii RNA. Still other conjugated chemical moieties enhance cellular uptake of the copolymer (e.g. polylysine). Still others, direct delivery or uptake of the copolymer to specific tissues or cell types. These different groups are either conjugated to terminal hydroxyl groups of the copolymer, or to internal phosphates. Additionally, they can be conjugated to linkers attached to terminal or internal sugar or base residues, or to linkers inserted between nucleotides in the chain (see review (Goodchild, *Bioconjugate Chem.* 1: 165–187 (1990)).

Cross-linking and alkylating groups include the following:

1. nitrogen mustard derivatives (Knorre & Vlassov, *Progress in Nucleic Acids Research and Molecular Biology* 32: 291–320 (1995))
2. diazomethane derivatives (Nakatani et al., *J. Am. Chem. Soc.* 119: 7626–7635 (1997))
3. iodoacetamido or bromoacetamido functions conjugated to various sites on nucleoside bases through spacer chains (Meyer et al., *J. Amer. Chem. Soc.* 111: 8517–8519 (1989); Kido et al., *Nucleic Acids Res.* 20: 1339–1344 (1992); Coleman & Pires, *Nucleic Acids Res.* 25: 4771–4777 (1997))
4. phenazine di-N-oxide (Nagai & Hecht, *J. Biol. Chem.* 266: 23994–24002 (1991))
5. naphthoquinone that is photoactivated (Chatterjee & Rokita, *J. Amer. Chem. Soc.* 112: 6397–6399 (1990)) or activated to a quinone methide by cytochrome c reductase (Chatterjee & Rokita, *J. Amer. Chem. Soc.* 113: 5116–5117 (1991))
6. porphyrins (Le Doan et al., *Bioconjugate Chem.* 1: 108–113 (1990)) and palladium (II)-coproporphyrin following photoactivation (Fedorova et al., *FEBS Letters* 259: 335–337 (1990))
7. 5-methyl-$N^4$, $N^4$-ethanocytosine that can be used in place of cytosine (Webb & Matteucci, *Nucleic Acids Res.* 14: 7661–7674 (1986))
8. psoralen that is photoactivated (Bhan & Miller, *Bioconjugate Chem.* 1: 82–88 (1990))

Groups conjugated to copolymers which catalyze hydrolysis of hybrid bound RNA chains include:

1. staphylococcal nuclease (Zuckermann et al., *J. Amer. Chem. Soc.* 110: 1614–1615 (1988))
2. imidazole and primary amines (Ushijima et al., *Bba. Gen. Subjects* 1379: 217–223 (1998)) or diamines (Reynolds et al., *Nucleic Acids Res.* 24: 760–765 (1996))
3. histamine (Hovinen et al., *J. Org. Chem.* 60: 2205–2209 (1995))

Chelating groups conjugated to the copolymer promote metal promoted catalysis of RNA hydrolysis. Some examples include:

1. iminodiacetate (Matsumura et al., *J. Chem. Soc., Chem. Commun.* 1994: 2019–2020 (1994))
2. phenanthroline (Perrin et al., *Biochemistry* 33: 3848–3854 (1994))
3. 2,2'-bipyridine and 2,2':6',2"-terpyridine (Bashkin et al., *J. Org. Chem.* 61: 2314–2321 (1996))
4. texaphyrin (Magda et al., *J. Am. Chem. Soc.* 119: 2293–2294 (1997))
5. EDTA (Joseph et al., *Science* 278: 1093–1098 (1997))
6. porphyrins (Sigman, *Biochemistry* 29: 9097–9105 (1990))
7. bleomycin (Bergstrom & Gerry, *J. Amer. Chem. Soc.* 116: 12067–12068 (1994))
8. 2,6-pyridinedicarboxylate (Bergstrom & Gerry, *J. Amer. Chem. Soc.* 116: 12067–12068 (1994))
9. 2,2'-dipocylylamine (Bergstrom & Gerry, *J. Amer. Chem. Soc.* 116: 12067–12068 (1994))

The catalytically active sites from hammerhead and hairpin ribozymes can be engineered into the copolymers to generate artificial ribozymes which catalyze the cleavage of the complementary Ii RNA (Santoro and Joyce, *A general purpose RNA-cleaving DNA enzyme* 94: 4262–4266 (1997)).

In nature, a number of ribozymes play a role in site-specific cleavage of RNA during RNA processing. These can be broken into several types, including group I, group II, hammerhead, hairpin and HDV ribozymes, in addition to other less well characterized forms (Cech & Bass, *Annu. Rev. Biochem.* 55: 599–629 (1986)). The development of catalytically active antisense oligonucleotides has been reviewed by Christoffersen & Marr, *J. Med. Chem.* 38: 2023–2037 (1995). Alternatively, the same principles can be used to engineer ribozymes into reverse gene constructs, which are discussed in detail below.

Examples of intercalating groups conjugated to copolymers include:

1. fluorescent intercalator (Endo & Komiyama, *J. Org. Chem.* 61: 1994–2000 (1996))
2. acridine (Lancelot et al., *Biochemistry* 24: 2521–2529 (1985); Asseline et al., *Proceedings of the National Academy of Science USA* 81: 3297–3301 (1984); Asseline et al., *EMBO J.* 3: 795–800 (1984); Asseline et al., *J. Biol. Chem.* 260: 8936–8941 (1985))
3. anthraquinone (Deshmukh et al., *Bioconjugate Chem.* 6: 578–586 (1995))
4. daunorubicin (Timofeev et al., *Tetrahedron. Lett.* 37: 8467–8470 (1996))
5. methidium (Timofeev et al., *Tetrahedron. Lett.* 37: 8467–8470 (1996))
6. oxazole yellow (Ishiguro et al., *Nucleic Acids Res.* 24: 4992–4997 (1996))
7. phenanthrine (Puri et al., *Tetrahedron* 53: 10409–10432 (1997))
8. pyrene (Mann et al., *Bioconjugate Chem.* 3: 554–558 (1992))

Groups conjugated to promote cellular uptake of a copolymer include:

1. fusogenic and other peptides that translocate through biological membranes (Bongartz et al., *Nucleic Acids Res.* 22: 4681–4688 (1994); Allinquant et al., *J. Cell. Biol.* 128: 919–927 (1995); Chaloin et al., *Biochem. Biophys. Res. Commun.* 243: 601–608 (1998))
2. polylysine (Degols et al., *Antisense Research and Development* 2: 293–301 (1992))
3. cholesterol and cholic acid (Chow et al., *Antisense Research and Development* 4: 81–86 (1994))

Complexes, adjuvants and formulations used to increase cellular uptake of a copolymer or other forms of a specific regulator of Ii include:

1. liposomes (Zelphati & Szoka, *Pharmaceut. Res.* 13: 1367–1372 (1996); Juliano & Akhtar, *Antisense Research and Development* 2: 165–176 (1992))
2. Liposomes containing inactivated Sendai virus or other fusion proteins (Kitajima et al., *J. Biol. Chem.* 272: 27099–27106 (1997); Morishita et al., *Gene* 149: 13–19 (1994); Kitajima et al., *Arthritis. Rhem.* 40: 2118–2127 (1997))
3. cyclodextrin (Zhao et al., *Antisense. Res. Dev.* 5: 185–192 (1995))
4. fusogenic peptides (Hughes et al., *Pharmaceut. Res.* 13: 404–410 (1996); Morris et al., *Nucleic Acids Res.* 25: 2730–2736 (1997))
5. cationic lipids (Zelphati & Szoka, *Pharmaceut. Res.* 13: 1367–1372 (1996); Capaccioli et al., *Biochem. Biophys. Res. Commun.* 197: 818–825 (1993))
6. a peptide comprising a part that binds to nucleic acids and another part that binds to the widely expressed integrin receptor on cell surfaces (Bachmann et al., *J. Molecular Med. Imm.* 76: 126–132 (1998))

7. streptolysin-O (Giles et al., *Nucleic Acids Res.* 26: 1567–1575 (1998))
8. polyethylenimine (Boussif et al., *Proc. Natl. Acad. Sci. USA* 92: 7297–7301 (1995))
9. cationic phosphonolipids (Le Bolc'h et al., *Tetrahedron Lett.* 36: 6681–6684 (1995))
10. dendrimers (Hughes et al., *Pharmaceut. Res.* 13: 404–410 (1996))
11. cationic facial amphiphiles (Walker et al., *Proc. Natl. Acad. Sci. USA* 93: 1585–1590 (1996))

Groups conjugated to copolymers which promote selective uptake into a specific cell type or tissue include:

1. neoglycoproteins to direct uptake to monocytes and macrophages that have membrane lectins that internalize glycoproteins (Bonfils et al., *Nucleic Acids Res.* 20: 4621–4629 (1992))
2. a peptide that serves as a nuclear transport signal (Delatorre et al., *Tetrahedron. Lett.* 35: 2733–2736 (1994))
3. cholesterol, cholic acid and a tetrapeptide, fMFLY, to target neutrophils (Chow et al., *Antisense Research and Development* 4: 81–86 (1994))
4. mannose to target macrophages that have mannose specific surface lectins (Akhtar et al., *Tetrahedron Lett.* 36: 7333–7336 (1995))
5. asialoglycoprototein to target the liver (Rajur et al., *Bioconjugate Chemistry* 8: 935–940 (1997))
6. peptide analog of insulin-like growth factor 1 to increase uptake by cells that express insulin growth factor 1 receptor (Basu & Wickstrom, *Bioconjugate Chemistry* 8: 481–488 (1997))
7. interleukin-1β to increase uptake by cells that express the receptor for interleukin-1β

Complexes, adjuvants and formulations used to direct uptake of copolymers to specific cell or tissue types include:

1. oligonucleotide complexed with polylysine conjugated to asialo-orosomucoid or an asialoglycoprotein that targets liver specific asialoglycoprotein receptor (Bunnell et al., *Somat. Cell. Mol. Genet.* 18: 559–569 (1992); Wu & Wu, *J. Biol. Chem.* 267: 12436–12439 (1992); Lu et al., *J. Nucl. Med.* 35: 269–275 (1994))
2. oligonucleotides complexed with polylysine conjugated to transferrin to target cells that express high levels of transferrin receptor (Citro et al., *Proc. Natl. Acad. Sci. USA* 89: 7031–7035 (1992))
3. oligonucleotide complexed with polylysine conjugated to folic acid to target rapidly dividing cells that over express receptors for vitamins oligonucleotide (Citro et al., *British J. of Cancer* 69: 463–467 (1994); Leopold et al., *Blood* 85: 2162–2170 (1995))
4. Mannose conjugated with streptavidin binds to biotinylated oligonucleotides to direct uptake into macrophages that have mannose specific surface lectins (Bonfils et al., *Bioconjugate Chem.* 3: 277–284 (1992))
5. galactosylated polyethylenimine to target hepatocytes (Zanta et al., *Bioconjugate Chem.* 8: 839–844 (1997))

In a preferred embodiment, the copolymer is conjugated to one or more chemical moieties, described above, to improve the pharmacological properties or toxicity profile of the copolymer. Pharmacological properties which can be effected include, but are not limited to, bioavailability, stability, half-life in serum and/or in physiologically relevant compartments, toxicity, and competing biological effects which may or may not be deleterious. For example, physical properties of copolymers are altered by conjugation of lipophilic or charged moieties such as cholesterol (Ojwang et al., *J. Acq. Immun. Defic. Syndrome* 7: 560–570 (1994)). This alteration impacts the biological properties of the copolymer (Chow et al., *Antisense Research and Development* 4: 81–86 (1994); Demirhan et al., *Virus Genes* 9: 113–119 (1995)). Another example is a copolymer conjugated to biotin which is then allowed to bind to streptavidin. This product is cleared by the kidneys over 10 times slower than the unconjugated oligonucleotide reducing the systemic clearance rate by 50%, and redirecting more copolymer to the liver (Kang et al., *Drug Metab. Dispos.* 23: 55–59 (1995)).

The other type of specific regulator which forms a duplex molecule with the Ii RNA to inhibit translation is an expressible reverse gene construct. In the present invention, such a reverse gene construct is an expressible DNA construct, the expression of which directs synthesis or translation of a RNA molecule which is complementary to a segment of the RNA molecule which encodes wild-type Ii. When coexpressed in an Ii producing cell, the RNA product of the reverse gene construct can hybridize to the RNA encoding Ii thereby forming a duplex structure. The formation of this duplex structure inhibits the translation of the mRNA which encodes Ii, thereby reducing Ii protein levels in the cell.

Preferably, the reverse gene construct is synthesized using cDNA, or a fragment thereof, encoding Ii from an organism corresponding to the cell type in which the reverse gene construct will be expressed. The methods and compositions of the present invention are applicable to mammalian systems in general. cDNA encoding the Ii protein has been produced from mRNA isolated from a variety of mammalian systems and the nucleic acid sequence has been determined (Singer et al., *EMBO J.* 3: 873–877 (1984); Strubin et al., *EMBO J.* 3: 869–872 (1984); Henkes et al., *Nucl. Acids Res.* 16: 11822 (1988)). The mammalian genes encoding Ii have been determined to be highly conserved. For example, the cDNA sequence encoding murine and human Ii have been determined to be approximately 85% homologous. The degree of conservation between the murine and rat sequences is greater than 90% (Henkes et al., *Nucl. Acids Res.* 16: 11822 (1988)). In light of the high degree of conservation among mammalian Ii genes, cDNA libraries from virtually any mammalian system of interest could be screened with an Ii probe (e.g. human or murine in origin) to isolate the corresponding Ii gene.

The selection of an expression vector background for use in the construction of the reverse gene construct is influenced by the cell type in which expression is desired. A great variety of appropriate vectors are available and one of skill in the art would be able to select an appropriate vector from among the many available without the necessity for undue experimentation. Similarly, regulatory signals required for efficient expression are selected based on the cell type in which expression is desired. The requirements for such regulatory signals are well known in the art, and unrestricted sources for such signals are generally known.

In a preferred embodiment, the reverse gene construct is expressed from a viral expression vector. The viral expression vector being characterized by the ability to enhance transfection into mammalian cells. Such vectors include without limitation, the MFG retroviral vector, other retroviral vectors such as the pLJ, pEm, and alphaSGC vectors, and adenoviral vectors. Such vectors may have a particular utility to screen a number of reverse gene constructs in an assay system in order to identify particular constructs having a high efficiency of expression and function in a given cell type. In addition, such vectors may express proteins with the characteristic to enhance binding to, and/or uptake by particular cell types. Such vectors may also be preferred because they contain transcriptional promoters which enhance expression of the reverse gene construct in mammalian cells as a general property, and/or in particular cell types, for example those which are isolated from cancers of a certain organ or tissue class.

A reverse gene construct may be produced by introducing an Ii cDNA, or fragment thereof into a suitable expression vector in reverse orientation, relative to the promoter, as compared to the wild-type orientation. In light of the fact that mRNA is known to assume a complex secondary structure which can interfere with its ability to hybridize to a complementary molecule, a full-length reverse gene construct (i.e., reverse gene construct which encodes a mRNA molecule which is complementary to the mRNA encoding Ii along its entire length) is not always the most efficient design. To develop more efficient constructs for Ii inhibition, it is often necessary to conduct routine experimentation in order to identify a less than full-length cDNA fragment which, when used in a reverse gene construct, is effective in inhibiting Ii synthesis. An example of such experimentation is detailed in the Exemplification section of this application.

In designing a less than full-length construct, it is often desirable to identify functionally significant regions of the mRNA encoding Ii, and design the reverse gene construct such that the mRNA encoded by the reverse gene construct is complementary with the functionally significant region. For example, functionally significant regions include regions involved in ribosome recognition of the mRNA, the translation initiation site, mRNA splice junctions and regions 3' of the translation termination codon which are required for polyadenylation.

In eukaryotic cells, the mechanism of initial ribosomal engagement with mRNA differs from the mechanism in prokaryotes. In eukaryotes, it is generally the 5'-most Met-specifying codons which are used as translation initiation points. The 5' end of eukaryotic mRNAs have a modified end comprising a methylated guanylate residue joined to the first unmodified nucleotide in a 5'-5' pyrophosphate linkage (often referred to as a 5' cap). Experiments have demonstrated, for example, that mRNAs lacking the 5' cap are not efficiently translated. Therefore, translation initiation in eukaryotes appears to involves recognition of the 5' cap followed by location of a consensus sequence surrounding the AUG codon. The consensus sequence for ribosomal recognition of a nearby protein coding sequence is "5'-ACCAUGG-".

The location of splice sites within primary transcripts can be determined by comparing the genomic DNA sequences (which encode the primary transcripts) with the corresponding cDNA sequence (produced from processed transcripts). Discontinuities identified in such a comparison mark intron/exon boundaries. Studies of such boundaries have revealed moderately conserved, short consensus sequences at the intron/exon boundaries and a tendency for a pyrimidine-rich region just upstream of the 3' splice site. In addition, universally conserved nucleotide bases are found at the first two (GU) and last two (AG) intron positions.

Polyadenylation requires the poly(A) signal, AAUAAA, and about 30 nucleotides downstream from the poly A addition site. Polyadenylation stabilizes the mRNA, thereby extending its half-life within the cell.

In the experiments described in the Exemplification section which follows, reverse gene constructs for the inhibition of Ii expression in murine cells were designed and tested. The murine Ii protein is comprised of 215 amino acid residues (Singer et al., $EMBO\ J.$ 3: 873–877 (1984)). Thus, a full-length cDNA encoding this molecule would be comprised of 645 base pairs of coding sequence.

In the Examples which follow, several reverse gene constructs were designed and tested. Several of them were found to inhibit Ii protein expression in SaI/CIITA cells. Inhibition of Ii protein expression (up to 60% of cells) was observed in transfectants by some but not all mIi reverse gene constructs. The reverse gene constructs listed in SEQ ID NOS: 68, 71, 72, 75, 77, 78, and 79 significantly inhibited Ii protein expression.

As discussed above, efficiency of inhibition of protein expression using a reverse gene construct is dependent, to a large extent on the secondary structure of the target mRNA. The experiments described herein indicate that the Ii protein is particularly susceptible to inhibition of expression by a reverse gene construct. This conclusion is based on the fact that several reverse gene constructs exhibited the ability to significantly inhibit Ii expression. Furthermore, the truncated versions of the full length reverse gene construct produced even higher inhibition. This experimental work, together with the known high degree of conservation between mammalian Ii genes, is considered a valid predictor of reverse gene construct activity in other mammalian systems, including human systems.

In an alternate embodiment, the specific regulator of Ii is a copolymer comprised of nucleotide bases which hybridizes specifically to the Ii gene. This hybridization blocks the transcription and/or regulation of expression of the Ii gene of the target cell. Hybridization can be through the formation of Hoogsteen pairs, when the complementary Watson-Crick pairing of nucleotide bases of the two anti-parallel strands of DNA are maintained. Alternately, the pairing of nucleotide bases of the therapeutic agent can be in an anti-parallel fashion with the nucleotide base sequence of one strand of the cellular DNA, through the formation of a 'D loop'. Appropriate copolymer compositions and methods of delivery to a cell are described above.

In another embodiment the specific regulator of Ii is an organic molecule of 20 to 1000 Daltons. The organic molecule inhibits Ii protein function by altering interactions of Ii protein with the MHC class II molecule in a manner to enhance binding of endogenous antigenic determinants to MHC class II molecules, for example in the endoplasmic reticulum of the target cell. Examples of organic molecules of the present invention include but are not limited to peptides, peptidomimetics, small organic molecules. Organic molecules which function as specific regulators of Ii are identified through programs for rational design based on crystallographic or NMR evidence for structure of the MHC class II molecules and Ii proteins. More specifically, interaction sites between the Ii protein and MHC class II molecules are identified and compounds which mimic peptidyl segments of either proteins, at the interaction site, are prepared and tested for disruption of formation of the MHC Class II/Ii protein complexes. Alternatively, such small organic molecules are identified through the preparation of combinatorial libraries of compounds or with multiple, systematically varied chemical groups. Such compounds are then tested in several types of assays. At an in vitro chemical level, the dissociation of Ii protein from MHC class II $\alpha,\beta$ proteins, in the presence or absence of specific cathepsins and other intracellular proteases are assayed. Candidate molecules from such assays are further tested for enhancement of presentation of endogenously synthesized antigenic determinants, for example, from hen egg lysozyme coded in a transfected gene format. Lead compounds are then assayed for in functional assays, for example enhancement of the induction of tumor immunogenecity in a cancer cell vaccine model discussed below.

In a preferred embodiment, the specific regulator of Ii protein expression or immunoregulatory function is formulated in a pharmaceutically acceptable carrier. The carrier has preferred properties with respect to, for example and without limitation, protection from denaturation, stability, adsorption to the surface of the target cell population by general physicochemical means and/or by a specific adherence to a cell surface receptor. The pharmaceutically acceptable carrier also may enhance delivery of the specific regulator of Ii to a population of cells.

In one embodiment, the pharmaceutically acceptable carrier is a liposome or vesicle preparation of one or more lipids and or lipopolysaccharide, which have one or more desired properties, for example, of protection, compartmentalization, or delivery to a targeted cell population.

In another embodiment, the pharmaceutically acceptable carrier enhances delivery of the specific regulator of Ii to a specific population of cells. An example of this is a formulation in which interaction of a molecule which is tethered to, adsorbed on, or otherwise adherent to the formulation, for example a liposome or vesicle preparation, which molecule has the property of binding to the surface of the target cell population, for example, through interaction with a complementary receptor molecule on the target cells.

Another aspect of the present invention relates to cells into which a specific regulator of Ii protein expression or immunoregulatory function has been introduced. Introduction of a specific regulator of Ii, described above, to an appropriate recipient cell can be achieved by a variety of methods. The method which is used depends upon the specific regulator to be delivered, the formulation of the specific regulator, and the recipient cell. These cells have several uses in disease therapy and in development of novel diagnostic and therapeutic reagents (antigenic peptides and their derivatives) from the epitopes presented by such cells.

An appropriate recipient cell is a cell which expresses MHC class II molecules and otherwise functions to present antigen through the MHC class II molecules. This cell can be either naturally occurring or alternatively generated from the manipulation of one or more cells, discussed below. Cells which express MHC class II molecules are herein referred to as MHC class II-positive. Cells which meet the above requirements are herein referred to as MHC class II-positive antigen presenting cells.

Naturally occurring functional antigen presenting cells express MHC class II molecules and other auxiliary functions required for the processing, trafficking, binding, and editing of antigenic peptides on their way toward incorporation into the MHC class II peptide binding site. In addition, such cells express cell surface interaction molecules, such as B7, CD24, CD40, interleukin receptors, and interleukins and other such proteins, which may be required for an optimal biological response upon recognition of an antigenic peptide in the context of MHC class II molecules. If not naturally occurring, expression of the required auxiliary functions may be induced in a cell, either through the use of cytokines such as interferon gamma or granulocyte macrophage colony stimulating factor, or through gene transfections using any of the above facilitators of the immune response. Such cells and cellular derivatives, and their progeny, are encompassed by the present invention.

One ultimate goal of the present invention is to produce a cell which displays a specific antigenic peptide in association with an MHC class-II protein. Accordingly, the recipient MHC class II-positive antigen presenting cell must express or otherwise contain this peptide. In a preferred embodiment, the MHC class II-positive antigen presenting cell is generated from the fusion of a cell containing antigen presenting machinery and the relevant MHC class II molecules, with a cell, or derivatives of that cell, which contain the antigenic peptide or determinant to which an immune response is desired. In most instances, the product is a fusion of a class of professional antigen presenting cells, such as dendritic cells, macrophages, B lymphocytes, or certain multipotent cells, and cells which express the antigenic epitopes of interest. Such cells expressing antigenic epitopes include, for example, malignant cells, virally infected or transformed cells, cells relevant to induction of an autoimmune response, and cells regulating the autoimmune response, for example through anti-idiotypic network mechanisms (e.g. expressing the T cell receptor (TCR) of pathogenic relevance in rheumatoid arthritis). The fusion product may be a grossly heterogeneous preparation of cells, either as freshly obtained ex vivo or after duplication in vitro. They may be either cell lines derived from such fusions in vitro, or clonal preparations derived from such cell lines.

Alternatively, the recipient MHC class II-positive antigen presenting cell is produced from the introduction of genetic material or protein derivatives from a cell carrying the desired antigenic epitopes, to a cell which naturally expressed both antigen presenting machinery and the relevant MHC class II molecules. For example, cDNA is synthesized from a preparation of polyadenylated mRNA from a cell. That cDNA preparation is transferred by established procedures to another cell in which synthesis of antigenic epitopes is desired. Methods of DNA transfer with a gene gun or other technique, are available and can be successfully applied by to one of skill in the art (U.S. Pat. No. 5,593,972 (1997); U.S. Pat. No. 5,643,578 (1997); U.S. Pat. No. 5,716,613 (1998); U.S. Pat. No. 5,741,486 (1998)). Additionally, genes for tumor-related or tumor-specific proteins, or segments of genes for such proteins, can be transferred into dendritic cells or another professional antigen presenting cell population of a patient, as disclosed by U.S. Pat. No. 5,627,025, (1997), the contents of which are herein incorporated. Cell populations generated from these methods can be used as a vaccine at the crudely heterogenous, cell line, or clonal level.

In one embodiment, the recipient MHC class II-positive antigen presenting cell is a malignant cell or contains components derived from a malignant cell. Such cells include but are not limited to carcinomas and other tumors of the stomach, colon or rectum, breast, lung, prostate, bladder, pancreas, and brain, and also melanoma, leukemia and lymphoma cells. In a preferred embodiment the cell expresses an idiotypic determinant in a cell surface receptor, for example in the context of MHC class I or MHC class II molecules. Such idiotypic determinants may be derived, for example, from immunoglobulins or T cell receptors and are presented by MHC molecules. That is, the antigenic determinant is truly tumor-specific since the idiotypic peptides are derived from cell clone-specific receptors. The immunoglobulin receptors of a B-lymphoid malignancy contain idiotypic peptide sequences at their combining sites for antigen. Such receptors and their idiotypic peptides are unique to those populations of cells.

In another embodiment, the recipient MHC class II molecule-antigen presenting cell is a nonmalignant cell. These cells include but are not limited to cells containing viruses, bacteria, parasites, or other pathogens. Also included are cells which function in the immune system, for example T cells, B cells, macrophages, dendritic cells and natural killer cells.

The cells described above have several uses in disease therapy and in the development of novel diagnostic and therapeutic reagents from the epitopes presented by such cells. Along these lines, the present invention also provides methods for the production of therapeutic reagents and therapeutic methods for the treatment of disease. One aspect of the present invention is a method for displaying an autodeterminant peptide, in association with an MHC class II protein, on the surface of a MHC class II-positive antigen presenting cell. An autodeterminant peptide is herein defined as a peptide which can be bound into the antigenic peptide binding site of MHC class II molecules, for presentation to T lymphocytes. Such peptides may be derived either from proteins synthesized within the antigen presenting cell itself, or from proteins transferred into the antigen presenting cell, for example by cell surface receptors for antigen or complement. The method comprises providing a MHC class II-positive antigen presenting cell, described in detail above, which contains a desired autodeterminant peptide. Once provided, a specific regulator of Ii protein expression or immunoregulatory function is introduced into the cell to effect the display of the autodeterminant peptide in association with the MHC class II protein. The specific regulator of Ii can be in any form previously described. In a preferred embodiment, the specific regulator of Ii is either a copolymer comprising nucleotide bases or is an expressible reverse gene construct. The cell into which such compositions are introduced can be either malignant or non-malignant, and either from an individual in whom a therapeutic effect is desired from immunization with endogenous determinants of such a treated cell or from another individual. In addition the cell into which such compositions are introduced can be a sample obtained either freshly from an individual or after culturing, including for the establishment of cell lines or clones. The specific regulator of Ii is preferably introduced into the recipient cell by electroporation.

In another aspect, the present invention provides a method for the therapeutic treatment of malignancy in a patient by enhancing immunological attack on the malignancy. This is accomplished through the generation and use of a tumor cell vaccine. A tumor cell vaccine is generated by manipulating cells which contain antigenic epitopes of a malignancy, to present the epitopes through MHC class II molecules, in an effort to prime the patient's immune system towards the malignancy. This type of therapy is accomplished by one of two approaches, 1) by an ex vivo approach, in which cells are manipulated in vitro to produce the tumor vaccine cells, and then introduced into the patient, and 2) by directly producing the tumor vaccine cells in vivo. In the first approach, the population of malignant cells can be obtained from a variety of sources. Such preparations can be from an unselected population of malignant cells obtained from a patient, with or without separation from accompanying normal cells, or cells obtained as cell lines, or as clones from such cell lines. Such cells are obtained from established malignant cell lines or explants of fresh malignant tissue, (e.g. colon or ovarian adenocarcinoma). If necessary, the obtained cell population can be expanded in vitro. Alternatively, non-malignant cells can be used.

Whatever the source, the cells must express or contain antigenic determinants of the malignancy which is to be treated. Additionally, if the cells do not naturally express a sufficient amount of MHC class II molecules, they must be induced to do so. This can accomplished by the methods described above.

Once the appropriate population of cells is obtained or generated, a specific regulator of Ii expression is introduced into the cells by the methods previously described, preferably by electroporation. After introduction of the specific regulator, the cells are generally further cultured for a period of time required for the inhibitor of Ii expression to exert its effect on suppressing Ii expression, for MHC class II charging with endogenous antigenic determinants, and thereafter for such complexes to become surface-expressed.

The treated cells are then introduced into the patient. Alternatively, a derivative of the treated cells is introduced into the patient. Introduction of the cells can be, for example, intravenously, subcutaneously, intraperitoneally, or intramuscularly. In a preferred embodiment, introduced cells are made replication incompetent (e.g. by radiation treatment or by fixation) prior to introduction into the patient.

Established protocols for cancer vaccine immunotherapy are discussed by Clements et al., *Immunol.* 149: 2391–2396 (1992); Baskar et al., *Cell. Immunol.* 155: 123–133 (1994); Baskar et al., *J. Exp. Med.* 181: 619–629 (1995); Hersey, *Drugs* 47: 373 (1994); and Pardoll, *Immunol. Today* 14: 310 (1993).

The second approach to the therapeutic treatment of malignancy in a patient, provided by the present invention, involves introduction of a specific regulator of Ii into accessible tumor cells, which are not removed from the patient, by administering the specific regulator of Ii to the patient in an amount sufficient to induce an anti-cancer immune response. Such a response is characterized by induction of the activity and/or number of T lymphocytes which effect the killing of cancer cells and/or regulate other cells to effect the killing of cancer cells. The amount required to induce an anti-cancer immune response will vary with each patient and specific malignancy. In one embodiment, the amount is between 10 $\mu$g and 100 mg daily.

Suitable avenues of administration include, but are not limited to intravenous infusion (e.g. via injection), infusion across skin or a mucosal surface (e.g. topical application), insertion with a gene gun after coating onto suitable carrier particles (e.g. colloidal gold). In particular, microinjection into visceral metastases by a radiologist using fluoroscopy to visualize the target tissue is a well described, standard methodology. Such administration can also be through infusion into body cavities, or into ascites fluid contained in such cavities, for example in the case of ovarian carcinoma. Through such methods the specific regulator of Ii contacts and is introduced into either primary or metastatic tumor cells, to enhance the MHC class II molecule presentation of endogenous tumor determinants, by the tumor cells to the immune system.

In one embodiment, the specific regulator of Ii is administered with a pharmaceutically acceptable carrier. In brief, there are well established methods to protect therapeutic oligonucleotides after systemic or regional infusion and to target delivery to and entry into selected cell populations. The method of systemic or regional treatment will be adapted to the tumor and its presentation. For example, ovarian cancer with abdominal metastases and ascites will be treated with intraperitoneal infusion of the oligonucleotide administered in an appropriate formulation to enhance uptake by the malignant cells. Those methods have been presented in the literature and patents cited herein or in U.S. Pat. No. 5,098,890 (1992); U.S. Pat. No. 5,273,745 (1993); U.S. Pat. No. 5,290,551 (1994); U.S. Pat. No. 5,637,483 (1997); U.S. Pat. No. 5,648,223 (1997); U.S. Pat. No. 5,679,647 (1997); U.S. Pat. No. 5,693,522 (1997); and U.S. Pat. No. 5,788,963 (1998), the pertinent contents of which are incorporated by reference.

Methods similar to those described above can be applied to prime the immune system of an individual towards non-malignant cells which are otherwise undesired. Another aspect of the present invention is a therapeutic method for treating a non-malignant condition in an individual by enhancing immunological attack on an undesired cell population of the individual. Cells from the undesired cell population are obtained, usually directly from the patient, and manipulated in vitro as previously described, to generate MHC class II-positive antigen presenting cells which contain antigenic determinants common to the undesired cell population. Once an appropriate recipient cell population has been generated, a specific regulator of Ii protein expression is introduced into the recipient cells to enhance MHC class II presentation of antigenic determinants, as described above. The preferred method of this introduction is electroporation. The cells are then re-introduced into the individual. This can be accomplished by methods described above. In a preferred embodiment, the cells are made replication incompetent prior to re-introduction into the individual, previously discussed.

Usually the undesired cell population is the cause or product of a disease. A population of cells harboring a virus or other intracellular pathogen is one example. Such cells express proteins which either are encoded by the pathogen or are elicited in response to the pathogen. A population of cells involved in a pathogenic immunological response is another example.

Cells harboring a virus or other intracellular pathogen express molecules specific to infection of the pathogen. Some upstream regulatory regions for host cell structural genes can be activated with transacting factors which are either encoded by the pathogen, or are elicited by transacting factors coded by the pathogen. Host cell proteins can also be elicited as a component of the immune response to the pathogen, for example, by cytokines. Such proteins, with either absolute or relative specificity for the infected cell can be processed and presented by the infected cell, or by host antigen presenting cells, for example, macrophages or dendritic cells. When cells presenting proteins of the pathogen or elicited in response to the pathogen are appropriately contacted by an antisense reagent targeting the Ii protein, additional antigenic determinants are presented through the MHC class II molecules leading to expansion of T helper cell clones which then augment the otherwise MHC class I-restricted immune response to the pathogen. This method enhances MHC class II presentation of additional viral determinants, or determinants absolutely or relatively specific to the virally infected cell. The induction of MHC class II restricted helper cells leads to enhanced destruction of the virus infected cells by killer T lymphocytes and to enhanced induction of therapeutic immunoglobulins. In this regard, only a portion of the virally infected cells need be treated with an Ii antisense therapeutic and reintroduced into the patient. Particularly in the case of Epstein-Barr virus infection of normal B cells, in which Ii has been demonstrated to be greatly overexpressed in part to suppress the anti-EBV immune response, would such treatment be effective in enhancing an anti-EBV immune response. Similarly, in the case of HIV-infected CD4+ T lymphocytes which can upon activation express MHC class II antigens, will an anti-HIV immune response be enhanced by treatment of those cells with an anti-Ii construct. Procedures for monitoring the effectiveness of the treatment can be adapted from currently existing procedures. Methods for introducing viral DNA into cells and tissues are provided by U.S. Pat. No. 4,689,320 (1987) and U.S. Pat. No. 5,620,896 (1997), the relevant contents of which are herein incorporated by reference.

In another embodiment, the undesired cell population comprises autoreactive T lymphocytes. Cells involved in a pathogenic immunological response also express antigenic determinants specific to that population. As such, autoimmune diseases mediated by autoreactive T lymphocytes can be treated with the compositions and methods of this invention. Pathogenic T cells expressing MHC Class II molecule present, through those molecules, idiotypic peptides of their TCR. By using the above described methods, such cell populations can be used to induce an immune response of the patient against the pathogenic T cells. The methods are adapted from those described above for the preparation of a cancer cell vaccine. These methods specifically include, without limitation, the expansion in culture of the pathogenic T cells for the preparation of a T cell vaccine, and the transfection of another cell population, for example, dendritic cells, with a nucleic acid copolymer coding for a chain or segment of the TCR. The induction of MHC class II restricted helper cells leads to enhanced destruction of the pathogenic T cells, by other killer T lymphocytes. In this regard, only a portion of the pathogenic T cells, or a culture or clone thereof, needs be treated with an Ii antisense therapeutic and reintroduced into the patient.

For example, rheumatoid arthritis has been proposed to be mediated by destructive effects from cytotoxic T cells directed to antigens localized in inflamed joints. Such cytotoxic T cells have unique T cell receptors (TCR), which can be processed and presented to the immune system. Enhancing the immune response of other T cells to those TCR-derived, idiotypic peptides will improve the clinical status of patients with rheumatoid arthritis. To the extent that such pathological T lymphocytes express MHC class II molecules, introduction of a specific regulator of Ii protein expression will lead to priming of a helper T cell response against epitopes in the relevant TCR. As discussed above, in connection with the generation of a recipient MHC class II-positive antigen presenting cell, such therapies can also be effected by enhanced dendritic cell licensing. This mode of therapy includes, without limitation, isolation of T cell populations, and transfection of TCR genes into dendritic cells, as discussed above.

Procedures for monitoring the effectiveness of the treatment can be adapted from preexisting procedures for monitoring treatments of autoimmune diseases. Such relevant methods are either presented in the literature including that cited herein, or have been presented or reviewed by U.S. Pat. No. 5,614,192 (1997) the relevant contents of which are herein incorporated by reference.

In another embodiment, therapeutic treatment of a patient with an autoimmune disease is accomplished with administration of a specific regulator of Ii expression at appropriate times in the course of the disease. That is, treatments are timed to down regulate responses to determinants relevant to the expanding toxic phase of an autoimmune response, rather than during the suppressor T cell-mediated resolution of an autoimmune response. Such timing of treatment schedules have been described, for example in the case of rat adjuvant arthritis, and experimental allergic encephalomyelitis. In this method, the specific regulator of Ii function is administered to the patient in an amount sufficient to induce an anti-disease immune response. An anti-disease immune response is characterized by reduction in the activity and/or number of T lymphocytes which effect the pathological immune response and/or induction in the activity and/or number of T lymphocytes which regulate the activity and/or number of cells effecting the pathological immune response. The amount required to induce an anti-disease immune response will vary with each patient and specific disease. In one embodiment, the amount is between 10 $\mu$g and 100 mg daily.

Suitable avenues of administration include for example, injection into a joint space, administration intravenously or into a body cavity, and topical application. The patient is monitored for the stage of progression of the disease, or of an acute exacerbation of the disease, in order in part to time the administration in a manner to induce suppression of the disease.

In one embodiment, the specific regulator of Ii function is administered to the patient with a pharmaceutically acceptable carrier to protect the compounds and/or enhance targeting to and uptake at certain tissues. There are well established methods to protect therapeutic oligonucleotides upon regional or systemic infusion and to target delivery to and entry into selected cell populations. The method of regional or systemic administration will be adapted to the autoimmune disease and its presentation. For example, acute inflammation of one knee joint by rheumatoid arthritis may be treated by infusion of a specific regulator of Ii expression or immunoregulatory function into that joint space. Methods relevant to administering copolymers, and other specific regulators of Ii functions are presented above and in the literature and patents cited herein. Such methods are either presented in the literature cited below or in U.S. Pat. No. 5,356,779 (1994); U.S. Pat. No. 5,672,473 (1997); U.S. Pat. No. 5,731,160 (1998); U.S. Pat. No. 5,736,507 (1998) the pertinent contents of the cited patents are incorporated by reference.

The present invention also provides methods for isolating an autodeterminant peptide from a cell. The autodeterminant peptide is obtained by inducing MHC class II antigen presentation of the autodeterminant peptide using methods described above, and then solubilizing and purifying the MHC class II molecules which will co-purify with the autodeterminant peptides with which they are associated.

The cell which contains the desired autodeterminant peptide is obtained freshly from a patient, or from a culture of such cells. If the cell is not naturally an antigen presenting cell, for example, does not express MHC class II molecules, it is manipulated in vitro to exhibit the required activities, by the procedures discussed above. Once a recipient antigen presenting cell is generated, a specific regulator of Ii protein expression, described above, is introduced into the cell, and the cell is incubated for a sufficient time to allow expression of the specific inhibitor and the resulting enhancement of MHC class II antigen presentation of the autodeterminant peptide. The cells are then solubilized by standard procedures, and the MHC class II molecules and associated autodeterminant peptides are purified from the solubilized cell. Purification procedures include, but are not limited to, immunopurification of detergent-solubilized, lectin-affinity enriched membrane proteins. The autodeterminant peptides are then released from the immunopurified MHC class II molecules, for example by acid treatment. Released autodeterminant peptides are then isolated and identified. Purification can be accomplished by high pressure liquid chromatography and identification through the use of a mass spectrometry. Putative autodeterminant peptide sequences are confirmed through chemical synthesis of such peptides, followed by physical chemical and biological analyses. Such methods are presented in the literature as reviewed by Urban et al. *Crit. Rev. Immunol.* 17: 387–397 (1997).

The present invention also finds application in the treatment of a pathogenic autoimmune response in a patient. More specifically, enhancement of endogenous antigen presentation during certain phases of an autoimmune disease cycle is stimulated in order to down regulate a pathogenic autoimmune response. It has been demonstrated, for example, in certain animal models of arthritis (e.g. rat adjuvant arthritis), that after an initial phase of aggressive development of disease, suppressor T lymphocytes, directed against the same antigenic determinants which initiated the pathogenic process, will then suppress those immune responses. During that second phase of down regulation of the disease process (clinically seen as an indicator of remission), therapeutic enhancement of presentation of endogenous autoantigens in cells by inhibition of Ii will down regulate the disease. Furthermore, Ii inhibition in cells lacking co-stimulatory signals, (e.g. cells without B7, or in which B7 expression is suppressed by treatment with B7 antisense constructs), will produce anergic responses.

A population of cells (e.g. T lymphocytes which express T cell receptors which are active in the pathological process, or target cells of the autoimmune disease process, or a virus infected cell) is first isolated from the individual using standard techniques. If necessary, MHC class II molecules are induced in such cells by the techniques described above. The population of cells is then treated with a specific regulator of Ii protein expression. The cells are then solubilized and the MHC class II molecules and associated peptide are purified, for example by immunoprecipitation with monoclonal antibodies to the MHC class II molecules. The peptides are isolated from the MHC class II molecules, for example by acid treatment, and characterized, for example, after separation by high performance liquid chromatography, individual peptides are assayed by mass spectrometry. The sequence of a peptide is deduced from its ion fragmentation pattern in a mass spectrograph, and confirmed through analysis of spectrometry of synthetic peptides with the deduced sequence. Biological assays can further confirm the relevance of the synthetic peptide to the disease process, and its resolution. One or more synthetic forms, or homologs, of the identified peptides are then introduced into the patient, or other patients with the same pathological process, to effect a clinical alteration. Those treated patients are monitored for signs of remission.

Methods relevant to this procedure are presented in the literature cited herein or by U.S. Pat. No. 5,356,779 (1994); U.S. Pat. No. 5,672,473 (1997); U.S. Pat. No. 5,736,507 (1998); and U.S. Pat. No. 5,773,570 (1998), the pertinent contents of which are herein incorporated by reference.

A significant advantage of the above disclosed methods is that the transient or occasional use of the disclosed compositions leads to a priming of the immune system to disease-specific or disease-related determinants. After such a priming event, the immune system, without additional antisense treatments, is capable of rejecting either the tumor or the pathogenic, autoreactive T cell. In contrast, in most current applications of antisense therapeutics for the control of disease (e.g. viral diseases such as HIV), upon discontinuing the antisense drug, the disease (or virus) rebounds. Another preferred value of this method, is that induction of an anti-disease priming of the immune response can be pursued with either in vivo or ex vivo use of the disclosed antisense compositions.

Another aspect of the present invention relates to genetic therapy of an individual to treat a tissue-specific autoimmune disorder by increasing the Ii protein in tissues in which the autoimmune destruction is incited. This therapeutic approach is a conceptual mirror image of the applications presented above which decrease Ii protein expression to enhance MHC class II molecule presentation of autodeterminants. Conversely, this method results in an increased presence of the Ii protein during a cellular activating event. In such events, increased expression of MHC class II alpha and beta chains without concomitant increased expression of the Ii protein leads to enhanced presentation of autoantigens. This enhanced presentation of autoantigens leads to autoimmune responses which damage tissue. Therapeutically increasing the Ii in the tissue decreases the MHC class II molecule presentation of endogenous antigen, minimizing the autoimmune reaction and, in turn, tissue destruction. Ii protein is increased in the target tissue by increasing the constitutive expression of Ii. This is accomplished by introducing an Ii gene which is under the control of a promoter which is active in the target tissue cells. Preferably, the promoter is tissue specific, that is, is minimally active in non-target tissues. The Ii gene and promoter is provided in the form of an expression construct. Suitable expression constructs (e.g. viral vectors) and methods appropriate for the introduction of the expression construct into the patient's cells are presented above. Procedures and compositions which are common to various methods of gene therapy should be selected in accordance with obtaining a useful clinical result.

This method can be used to treat the disease diabetes mellitus, which results in the destruction of pancreatic beta cells. Insertion of the Ii gene under the control of the insulin promoter into a susceptible individual leads to enhanced expression of Ii protein in pancreatic beta cells. Treatment results in the protection of the pancreatic beta cells from autoimmune induced destruction. Additionally, the above method can be used to treat forms of thyroiditis, which lead to the destruction of thyroid follicular cells. Insertion of the Ii gene under the control of the thyroglobulin promoter will lead to enhanced expression of Ii in thyroid follicular cells, protecting them from autoimmune induced destruction.

Exemplification

EXAMPLE 1
Identification of Ii RNA Sites Hybridizing with Antisense Oligonucleotides The action of ribonuclease H to cleave RNA at sites which are hybridized to DNA was used to identify sites of Ii RNA which hybridized with antisense oligonucleotides. A series of deoxyoligonucleotides, each containing 18 bases in a sequence complementary, in a head-to-tail fashion, to a segment of Ii RNA in the staggered, overlapping pattern (Table 1) was used in the hybridization assay. RNA was transcribed and labeled at the 5'-end with $^{32}$P. Samples of this $^{32}$P-labeled Ii mRNA were incubated separately with each oligonucleotide, in the presence of ribonuclease H. Oligonucleotides hybridizing to the RNA directed the RNase H to cleave the RNA in the region of hybridization. The site of cleavage was indicated by the length of the labeled product, measuring from the 5'-end of the RNA. Reaction products were analyzed by polyacrylamide gel electrophoresis and autoradiography (Table 2). Some, but not all of the oligonucleotides effectively hybridized to the RNA, as indicated by the variable generation of cleavage products. No cutting of the Ii RNA was observed either in the absence of any oligonucleotide, in the presence of oligonucleotides, but lacking RNase H, or in the presence of a sense oligonucleotide control (SEQ ID NO:46) or an antisense oligonucleotide with one internal deletion (SEQ ID NO:43, SEQ ID NO:44 and SEQ ID NO:45). Oligonucleotide sequences yielding strongest cleavage were re-synthesized with phosphorothioate linkages for additional studies of antisense potency, presented in Examples 3, 4, and 5.

This study was performed using mouse Ii P31 mRNA, but similar procedures for analysis of hybridization sites are applicable to any species of RNA.

TABLE 1

Sequence of antisense phosphodiester oligonucleotides used in RNase H mapping experiment.

| SEQ ID NO: | SEQUENCE | NUCLEOTIDE POSITION |
|---|---|---|
| 5 | 5'- CAT GTT ATC CAT GGA CAT | 318–301 |
| 6 | 5'- CAT GGA CAT TGG ACG CAT | 309–292 |
| 7 | 5'- TGG ACG CAT CAG CAA GGG | 300–283 |
| 8 | 5'- CAG CAA GGG AGT AGC CAT | 291–274 |
| 9 | 5'- AGT AGC CAT CCG CAT CTG | 282–265 |
| 10 | 5'- CCG CAT CTG GCT CAC AGG | 273–256 |
| 11 | 5'- GCT CAC AGG TTT GGC AGA | 264–247 |
| 12 | 5'- TTT GGC AGA TTT CGG AAG | 255–238 |
| 13 | 5'- TTT CGG AAG CTT CAT GCG | 246–229 |
| 14 | 5'- CTT CAT GCG AAG GCT CTC | 237–220 |
| 15 | 5'- AAG GCT CTC CAG TTG CAG | 228–211 |
| 16 | 5'- CAG TTG CAG GTT CTG GGA | 219–202 |
| 17 | 5'- GTT CTG GGA GGT GAT GGT | 210–193 |
| 18 | 5'- GGT GAT GGT CAG CTT GTC | 201–184 |
| 19 | 5'- CAG CTT GTC TAG GCG GCC | 192–175 |
| 20 | 5'- TAG GCG GCC CTG TTG CTG | 183–166 |
| 21 | 5'- CTG TTG CTG GTA CAG GAA | 174–157 |
| 22 | 5'- GTA CAG GAA GTA AGC AGT | 165–148 |

TABLE 1-continued

Sequence of antisense phosphodiester oligonucleotides used in RNase H mapping experiment.

| SEQ ID NO: | SEQUENCE | NUCLEOTIDE POSITION |
|---|---|---|
| 23 | 5'- GTA AGC AGT GGT GGC CTG | 156–139 |
| 24 | 5'- GGT GGC CTG CCC AGC CAA | 147–130 |
| 25 | 5'- CCC AGC CAA GAG CAG AGC | 138–121 |
| 26 | 5'- GAG CAG AGC CAC CAG GAC | 129–112 |
| 27 | 5'- CAC CAG GAC AGA GAC ACC | 120–103 |
| 28 | 5'- AGA GAC ACC GGT GTA CAG | 111–94 |
| 29 | 5'- GGT GTA CAG AGC TCC ACG | 102–85 |
| 30 | 5'- AGC TCC ACG GCT GCA CCT | 93–76 |
| 31 | 5'- GCT GCA CCT TTC TGG CTC | 84–67 |
| 32 | 5'- TTC TGG CTC TCT AGG GCG | 75–58 |
| 33 | 5'- TCT AGG GCG GTT GCC CAG | 66–49 |
| 34 | 5'- GTT GCC CAG TAT GGG CAA | 57–40 |
| 35 | 5'- TAT GGG CAA CTG TTC ATG | 48–31 |
| 36 | 5'- CTG TTC ATG GTT AGA GAT | 39–22 |
| 37 | 5'- GTT AGA GAT GAG GTC GCG | 30–13 |
| 38 | 5'- GAG GTC GCG TTG GTC ATC | 21–4 |
| 39 | 5'- GCG TTG GTC ATC CAT GGC | 15—3 |
| 40 | 5'- TTG GTC ATC CAT GGC TCT | 12—6 |
| 41 | 5'- GTC ATC CAT GGC TCT AGC | 9—9 |
| 42 | 5'- CAC AGG CGC TGC TGC TGC | -23—40 |
| 43 | 5'- ATC CAT GGC TCT AGC C_CT<br>(5'- ATC CAT GGC TCT AGC CTC)*<br>(SEQ ID NO:2) | 6—13 (-11 deleted)<br>( 6—12) |
| 44 | 5'- TCT AGC C_CT AGT TTT TCC<br>(5'- TCT AGC CTC TAG TTT TTC)*<br>(SEQ ID NO:3) | -4—22 (-11 deleted)<br>( -4—21) |
| 45 | 5'- AGT TTT T_CC CAC AGG CGC | -14—31 (-20 deleted) |
| 46 | 5'- ATG GAT GAC CAA CGC GAC | 1–18 (sense) |
| 47 | 5'- CTA GTT TTT CCC ACA GGC | -12—29 |
| 48 | 5'- CTG CTG CTG TTG CTG CTG | -40—57 |

Ii mRNA sequence (Koch, N. et al. *EMBO J.* 6: 1677–1683, (1987)) is numbered so as the A of the first AUG codon is nucleotide 1 in the oligonucleotide SEQ ID NO:39, SEQ ID NO:40, SEQ ID NO:41, SEQ ID NO:43 and SEQ ID NO:46. Included as negative controls were: oligonucleotides SEQ ID NO:43, SEQ ID NO:44, and SEQ ID NO:45, each with an internal deletion, and oligonucleotide SEQ ID NO:46 with a sense sequence orientation. *Native sequences for SEQ ID NO:43 and 44 (without deletion) are shown in brackets and were used in subsequent experiments.

TABLE 2

RNase H mapping of accessible sites for mouse Ii antisense oligonucleotides.

| OLIGONUCLEOTIDE | NUCLEOTIDE POSITION | Signal |
|---|---|---|
| SEQ ID NO: 5 | 318–301 | – |
| SEQ ID NO: 6 | 309–292 | + |
| SEQ ID NO: 7 | 300–283 | + |
| SEQ ID NO: 8 | 291–274 | ± |
| SEQ ID NO: 9 | 282–265 | – |
| SEQ ID NO: 10 | 273–256 | ± |
| SEQ ID NO: 11 | 264–247 | +++ |
| SEQ ID NO: 12 | 255–238 | + |
| SEQ ID NO: 13 | 246–229 | + |
| SEQ ID NO: 14 | 237–220 | – |
| SEQ ID NO: 15 | 228–211 | – |
| SEQ ID NO: 16 | 219–202 | + |
| SEQ ID NO: 17 | 210–193 | + |
| SEQ ID NO: 18 | 201–184 | +++ |
| SEQ ID NO: 19 | 192–175 | – |
| SEQ ID NO: 20 | 183–166 | – |
| SEQ ID NO: 21 | 174–157 | – |

TABLE 2-continued

RNase H mapping of accessible sites
for mouse Ii antisense oligonucleotides.

| OLIGONUCLEOTIDE | NUCLEOTIDE POSITION | Signal |
|---|---|---|
| SEQ ID NO: 22 | 165–148 | ++ |
| SEQ ID NO: 23 | 156–139 | ± |
| SEQ ID NO: 24 | 147–130 | – |
| SEQ ID NO: 25 | 138–121 | – |
| SEQ ID NO: 26 | 129–112 | – |
| SEQ ID NO: 27 | 120–103 | ++ |
| SEQ ID NO: 28 | 111–94 | +++ |
| SEQ ID NO: 29 | 102–85 | – |
| SEQ ID NO: 30 | 93–76 | + |
| SEQ ID NO: 31 | 84–67 | ++ |
| SEQ ID NO: 32 | 75–58 | +++ |
| SEQ ID NO: 33 | 66–49 | – |
| SEQ ID NO: 34 | 57–40 | – |
| SEQ ID NO: 35 | 48–31 | – |
| SEQ ID NO: 36 | 39–22 | ± |
| SEQ ID NO: 37 | 30–13 | +++ |
| SEQ ID NO: 38 | 21–4 | +++ |
| SEQ ID NO: 39 | 15—3 | +++ |
| SEQ ID NO: 40 | 12—6 | +++ |
| SEQ ID NO: 41 | 9—9 | – |
| SEQ ID NO: 42 | –23—40 | – |
| SEQ ID NO: 43 | 6—13 (–11 deleted) | – |
| SEQ ID NO: 44 | –4—22 (–11 deleted) | – |
| SEQ ID NO: 45 | –14—31 (–20 deleted) | – |
| SEQ ID NO: 46 | 1–18 (sense) | – |
| No oligo | | – |
| No RNase H | | – |

The antisense oligonucleotide sequence ID numbers, their nucleotide starting positions in Ii mRNA and intensity of products as judged on a scale of –, + to +++, are given for each oligonucleotide.

Experimental

Compounds. Phosphodiester deoxyoligonucleotides were synthesized by Integrated DNA Technologies, Inc. (Coralville, Iowa). The SEQ ID NO:, nucleotide sequence and nucleotide number in Ii mRNA of each oligonucleotide are listed in Table 1.

Preparation of Ii mRNA. pBluescript KS plasmid containing murine Ii P31 cDNA was linearized with Xho I and transcribed in vitro using the T7—Ribomax large scale RNA production system (Promega, Madison, Wis.) according to the manufacturer's protocol. DNA template was removed by treatment with RQ1 RNase-free DNase (Promega, Madison, Wis.) and the RNA product was dephosphorylated with calf intestinal alkaline phosphatase (Promega, Madison, Wis.). The RNA was 5' end-labeled with [$\gamma$-$^{32}$P] ATP using T4 polynucleotide kinase (Promega, Madison, Wis.). All procedures were performed according to the standard molecular biological techniques (Sambrook, J., E. F. Fritsh, and T. Maniatis. 1990. *Molecular Cloning*, 2nd Ed. Cold Spring Harbor Laboratory Press, Cold Spring Harbor, N.Y.).

RNase H mapping of hybridization sites. $^{32}$P-labeled mouse Ii P31 mRNA (5×10$^5$ cpm) was mixed with 2 mg yeast tRNA in 1× RNase H buffer, heated at 70° C. for 3 minutes and cooled slowly to room temperature. Antisense oligodeoxynucleotide (0.2–1 pmol) was added and incubated at 37° C. for 30 minutes, followed by adding 0.5 unit of *E. coli* RNase H (Boehringer Mannheim, Indianapolis, Ind.) to give a final reaction volume of 10 ml. After incubation at 37° C. for 10 minutes, the reaction was stopped by adding 8 ml of electrophoresis loading buffer and heating at 90° C. for 5 minutes, followed by chilling on ice. 5 ml of the each preparation was subjected to electrophoresis at 50 watts for 2 hours in a 6% polyacrylamide gel, which was then exposed to X-ray film. The principal RNA cleavage products were identified by examination of autoradiography and their intensity is summarized in Table 2.

EXAMPLE 2

Optimal Conditions for Delivery of Oligonucleotides into Cells by Electroporation The study described here was performed with mouse SaI/CIITA cells but are applicable to any mammalian cell line.

Different conditions for electroporation of oligonucleotides into mammalian cells were tested to determine the conditions which produce maximal uptake with minimal cell damage. SaI/CIITA mouse sarcoma cells were subjected to electroporation using various combinations of voltage and capacitance. Fluorescein-labeled phosphorothioate oligonucleotide (SEQ ID NO:64) was used to allow detection and quantitation of oligonucleotide uptake. Control cells were subjected to electroporation in the absence of fluorescein-labeled oligonucleotide. The electroporated cells were cultured for an hour and then measured for viability by trypan blue dye exclusion. Uptake of the fluorescein-labeled oligonucleotide was measured with a fluorescence-activated cell sorter (FACS). A FACS drives individual cells through a laser beam which activates fluorescein labeled moieties. The intensity of fluorescence of each cell crossing the beam is measured with photomultiplier tubes. Forward and side scatter of light from each cell is simultaneously measured in order to exclude dead or clumped cells. After analysis of, for example ten thousand cells, a computer-assisted presentation of the data as a two-dimension histogram is created where the ordinate is a linear scale representing the number of cells detected, and the abscissa is a logarithmic scale representing the quantitative fluorescence of each cell. The data from the electroporation optimization assay is presented in Table 3 as the percentage of positive cells which represents the percentage of all cells having a fluorescence intensity greater than those of control cells.

Maximum oligonucleotide uptake and cell viability occurred using 200 V and 1200 mF (Table 3A). Over 90% of the cells became maximally fluorescent under these conditions using 2 mM oligonucleotide (Table 3B).

TABLE 3

Optimal conditions for oligonucleotide uptake by electroporation.

| OLIGO | VOLTS | CAPACITANCE (mF) | POSITIVE CELLS | VIABILITY |
|---|---|---|---|---|
| A. | | | | |
| – | – | – | 1.0% | 75.9% |
| + | – | – | 53.8% | 72.1% |
| – | 200 | 1200 | 0.0% | 72.3% |
| + | 100 | 600 | 60.2% | 72.7% |
| + | 100 | 1200 | 75.0% | 70.5% |
| + | 100 | 1800 | 76.7% | 70.4% |
| + | 200 | 600 | 75.9% | 74.8% |
| + | 200 | 1200 | 80.1% | 73.6% |
| + | 200 | 1800 | 71.3% | 74.8% |
| + | 300 | 600 | 69.1% | 67.9% |
| + | 300 | 1200 | 52.0% | 53.9% |
| + | 300 | 1800 | 21.2% | 47.8% |
| B. | | | | |
| – | – | – | 0.4% | 54.1% |
| + | – | – | 49.3% | 70.9% |

TABLE 3-continued

Optimal conditions for oligonucleotide uptake by electroporation.

| OLIGO | VOLTS | CAPACITANCE (mF) | POSITIVE CELLS | VIABILITY |
|---|---|---|---|---|
| − | 400 | 1200 | 3.3% | 39.0% |
| + | 200 | 300 | 64.5% | 72.6% |
| + | 300 | 300 | 76.8% | 62.0% |
| + | 400 | 300 | 71.7% | 52.0% |
| + | 500 | 300 | 76.0% | 27.0% |
| + | 200 | 400 | 84.7% | 59.1% |
| + | 300 | 400 | 91.5% | 70.2% |
| + | 400 | 400 | 37.9% | 43.3% |
| + | 500 | 400 | 83.0% | 28.8% |
| + | 200 | 1200 | 90.2% | 81.8% |
| + | 300 | 1200 | 89.6% | 53.6% |
| + | 400 | 1200 | 84.3% | 31.9% |
| + | 500 | 1200 | 88.7% | 18.2% |

Two experiments were performed: A) with 0.017 micromolar fluorescein-labeled phosphorothioate oligonucleotide SEQ ID NO: 64 and 2.15 micromolar phosphodiester oligonucleotide, and B) with 2 micromolar fluorescein-labeled phosphorothioate oligonucleotide SEQ ID NO: 64.

Experimental

Compounds. Phosphorothioate antisense oligonucleotide SEQ ID NO:64 (see Table 5) used in these studies was 5' labeled with fluorescein. It was synthesized and HPLC purified by Integrated DNA Technologies, Inc. (Coralville, Iowa).

Cell culture. The SaI/CIITA mouse sarcoma cell line was maintained in Iscove's Modified Dulbecco's Medium (IMDM, JRH Biosciences, Lenexa, Kans.) supplemented with 5% FCS (FetalClone I, HyClone Laboratories, Logan, Utah), 2 mM L-glutamine, 200 U/ml penicillin and 200 mg/ml streptomycin at 37° C. and 5% $CO_2$ in a humidified atmosphere.

Electroporation. Cells were washed twice with and resuspended in RPMI-1640 medium without supplements. 2–5× $10^6$ cells in 500 μl medium containing various amount of 5'-fluorescein-labeled phosphorothioate oligonucleotide SEQ ID NO:64 was added into a 4 mm-gap cuvette, incubated on ice for 10 minutes and electroporated in an ElectroCell Manipulator ECM 600 system (BTX Inc., San Diego, Calif.). Cells were kept at room temperature for 10 minutes after electroporation, mixed with an equal volume of IMDM with 2×supplements and incubated at 37° C. in 5% $CO_2$ for 1 hour before analysis. Cell viability was measured by trypan blue dye exclusion. Oligonucleotide uptake was assessed with FACS analysis of cells which had been washed once with 0.2 M glycine, pH 4.4, twice with Hanks' buffered salts solution, and fixed with 2% formalin for 15 minutes on ice. Cell viability and the percentage of cells showing oligonucleotide uptake are shown in Table 3.

EXAMPLE 3

Specific Inhibition of Ii Expression in Cells by Phosphorothioate Antisense Oligonucleotides Optimal methods for antisense oligonucleotide incorporation, determined above, were used in an assay to determine the effect of Ii antisense oligonucleotides on Ii protein expression in a tumor cell line. The SaI/CIITA murine sarcoma cell line was used in these assays. These cells are stably transfected with a plasmid containing the gene for the MHC class II transcription activator factor CIITA, and express high levels of MHC class II and Ii proteins.

Thirteen sequences determined in Example 1 to strongly hybridized to murine Ii RNA were synthesized as phosphorothioate antisense oligonucleotides. These oligonucleotides were introduced into SaI/CIITA cells via electroporation. After incubation for 24 hours, cells were assayed for levels of Ii and MHC class II proteins using fluorescent antibodies. The presence of bound anti-MHC class II antibody or anti-Ii antibody was quantified with a FACS, as described in Example 2. Suppression of expression of either Ii protein or MHC class II molecules was measured as the percentage of antisense oligonucleotide-treated cells showing the same intensity of fluorescence as control Ii-negative and MHC class II-negative cells (the parental SaI sarcoma cells without CIITA transfection). This measurement is cell-numbered in terms of reflecting the fraction of cells with complete suppression of the indicated protein expression and thus might underestimate the levels of suppression since cells with partial suppression of Ii protein might not be counted.

Results of these assays, presented in Table 4, indicate that the different oligonucleotides each produce varying levels of Ii inhibition. The greatest activity was shown by oligonucleotide SEQ ID NO: 40 (Table 1), complementary to the AUG initiator region and oligonucleotide SEQ ID NO: 32 complementary to the first splice donor site in the Ii mRNA. Control reactions performed with sense oligonucleotide (SEQ ID NO: 46) or no oligonucleotide showed no inhibition. MHC class II protein expression was not affected in any of the cells, which demonstrates that the inhibition produced by the antisense oligonucleotides is specific for Ii expression.

Additional overlapping oligonucleotides were then synthesized to find the most active sequence to target these regions (Table 5). These oligonucleotides were assayed as before and examined for activity in Ii inhibition (Table 6A) as well as for cytotoxicity (Table 6B). The most active compound, SEQ ID NO:54, was complementary to the AUG initiator and also showed minimal effects on MHC class II expression, recovery and viability of the cells. The best compound in the first splice donor region is SEQ ID NO:62. An antisense oligonucleotide (SEQ ID NO:64) complementary to polyadenylation site in 3' untranslated region also showed some activity.

TABLE 4

Inhibition of Ii but not I-E expression by phosphorothioate antisense oligonucleotides

| Oligo | Ii NEGATIVE CELLS | | | | I-E NEGATIVE CELLS | | | |
|---|---|---|---|---|---|---|---|---|
| | % | | FOLD | | % | | FOLD | |
| SEQ ID NO: | AVE. | SD | AVE. | SD | AVE. | SD | AVE. | SD |
| NONE | 10.8% | 5.3% | 1.0 | 0.0 | 2.6% | 1.3% | 1.0 | 0.0 |
| 46 | 6.2% | 0.1% | 0.7 | 0.3 | 2.8% | 0.9% | 1.1 | 0.2 |
| 11 | 21.3% | 14.7% | 1.9 | 0.4 | 2.5% | 1.1% | 1.0 | 0.0 |
| 18 | 16.6% | 6.3% | 1.6 | 0.2 | 2.4% | 1.0% | 0.9 | 0.1 |
| 28 | 13.0% | 5.8% | 1.2 | 0.1 | 2.8% | 1.5% | 1.0 | 0.1 |
| 31 | 22.1% | 12.2% | 2.0 | 0.1 | 2.5% | 0.9% | 1.0 | 0.1 |
| 32 | 23.5% | 10.5% | 2.2 | 0.1 | 2.8% | 1.2% | 1.1 | 0.1 |
| 38 | 21.1% | 13.6% | 1.9 | 0.3 | 2.8% | 0.9% | 1.1 | 0.2 |
| 39 | 31.0% | 16.9% | 2.8 | 0.2 | 2.3% | 0.8% | 0.9 | 0.1 |
| 40 | 34.4% | 9.1% | 3.4 | 0.8 | 2.8% | 0.7% | 1.1 | 0.3 |
| 41 | 23.8% | 1.2% | 2.5 | 1.1 | 2.3% | 0.4% | 0.9 | 0.3 |
| 42 | 10.7% | 3.8% | 1.0 | 0.2 | 2.7% | 1.0% | 1.1 | 0.1 |
| 41 | 5.3% | 0.4% | 0.5 | 0.2 | 2.6% | 0.7% | 1.0 | 0.2 |
| 47 | 13.7% | 7.6% | 1.3 | 0.1 | 2.5% | 0.8% | 1.0 | 0.2 |
| 48 | 20.8% | 10.6% | 1.9 | 0.0 | 3.0% | 0.7% | 1.2 | 0.3 |

The average values and standard deviations (SD) of percentage of Ii and I-E negative cells, as well as the fold of the negative cells as compared with that of control cells treated in the absence of antisense oligonucleotide, from two independent experiments are reported.

TABLE 5

Antisense phosphorothioate oligonucleotides used to determine the most active compound at the sensitive sites.

| SEQ ID NO: | SEQUENCE | NUCLEOTIDE POSITION |
|---|---|---|
| 49 | 5'GTCGCGTTGGTCATCCAT | 18—1 |
| 50 | 5' TCGCGTTGGTCATCCATG | 17—1 |
| 51 | 5'  CGCGTTGGTCATCCATGG | 16—2 |
| 39 | 5'   GCGTTGGTCATCCATGGC | 15—3 |
| 52 | 5'    CGTTGGTCATCCATGGCT | 14—4 |
| 53 | 5'     GTTGGTCATCCATGGCTC | 13—5 |
| 40 | 5'      TTGGTCATCCATGGCTCT | 12—6 |
| 54 | 5'       TGGTCATCCATGGCTCTA | 11—7 |
| 55 | 5'        GGTCATCCATGGCTCTAG | 10—8 |
| 41 | 5'         GTCATCCATGGCTCTAGC | 9—9 |
| 56 | 5'CACGGCTGCACCTTTCTG | 88—71 |
| 57 | 5' CGGCTGCACCTTTCTGGC | 86—69 |
| 31 | 5'  GCTGCACCTTTCTGGCTC | 84—67 |
| 58 | 5'   TGCACCTTTCTGGCTCTC | 82—65 |
| 59 | 5'    CACCTTTCTGGCTCTCTA | 80—63 |
| 60 | 5'     ACCTTTCTGGCTCTCTAG | 79—62 |
| 61 | 5'      CTTTCTGGCTCTCTAGGG | 77—60 |
| 32 | 5'       TTCTGGCTCTCTAGGGCG | 75—58 |
| 62 | 5'        CTGGCTCTCTAGGGCGGT | 73—56 |
| 63 | 5'         GGCTCTCTAGGGCGGTTG | 72—54 |
| 64 | 5'GACAAGCTTGGCTGAGCA | 1276—1261 |

TABLE 6

Inhibition of Ii but not I-E expression by phosphorothioate antisense oligonucleotides II

A.

| Oligo SEQ ID NO: | Ii NEGATIVE CELLS | | | | I-E NEGATIVE CELLS | | | |
|---|---|---|---|---|---|---|---|---|
| | % AVE. | SD | FOLD AVE. | SD | % AVE. | SD | FOLD AVE. | SD |
| NONE | 1.6% | 0.5% | 1.0 | 0.0 | 1.6% | 0.7% | 1.0 | 0.0 |
| 49 | 10.8% | 0.7% | 7.2 | 1.8 | 1.8% | 1.4% | 1.0 | 0.4 |
| 50 | 8.6% | 4.1% | 5.4 | 1.0 | 1.5% | 1.0% | 0.8 | 0.3 |
| 51 | 6.3% | 1.6% | 4.4 | 2.4 | 1.6% | 1.1% | 1.0 | 0.2 |
| 39 | 12.7% | 5.1% | 8.0 | 0.8 | 1.5% | 0.9% | 0.9 | 0.2 |
| 52 | 15.2% | 9.1% | 9.3 | 0.3 | 1.5% | 0.9% | 0.9 | 0.1 |
| 53 | 15.6% | 4.9% | 10.0 | 0.1 | 1.4% | 0.8% | 0.9 | 0.2 |
| 40 | 15.1% | 5.1% | 9.7 | 0.3 | 1.7% | 1.1% | 1.0 | 0.3 |
| 54 | 19.9% | 5.5% | 12.8 | 0.3 | 1.4% | 1.0% | 0.8 | 0.3 |
| 55 | 13.6% | 2.4% | 8.9 | 1.2 | 1.5% | 0.8% | 0.9 | 0.1 |
| 41 | 9.7% | 3.3% | 6.2 | 0.2 | 1.4% | 0.9% | 0.8 | 0.2 |
| 56 | 6.1% | 3.1% | 3.8 | 0.8 | 1.7% | 1.2% | 1.0 | 0.3 |
| 57 | 8.9% | 5.5% | 5.4 | 1.9 | 1.5% | 0.6% | 1.0 | 0.0 |
| 31 | 7.4% | 4.2% | 4.5 | 1.3 | 1.5% | 0.9% | 0.9 | 0.2 |
| 58 | 8.2% | 4.5% | 5.1 | 1.3 | 1.8% | 0.8% | 0.9 | 0.1 |
| 59 | 7.8% | 4.7% | 4.8 | 1.5 | 1.8% | 1.1% | 1.1 | 0.2 |
| 60 | 8.0% | 3.8% | 5.0 | 0.9 | 1.5% | 1.1% | 0.9 | 0.3 |
| 61 | 5.1% | 1.7% | 3.2 | 0.1 | 1.7% | 0.8% | 1.0 | 0.0 |
| 32 | 9.1% | 5.7% | 5.5 | 2.0 | 1.4% | 0.7% | 0.9 | 0.0 |
| 62 | 14.1% | 8.4% | 8.6 | 2.8 | 1.5% | 1.0% | 0.9 | 0.2 |
| 63 | 6.6% | 4.3% | 4.0 | 1.6 | 1.7% | 1.1% | 1.0 | 0.2 |
| 64 | 7.4% | 1.0% | 4.9 | 0.9 | 1.4% | 0.9% | 0.9 | 0.2 |

B.

| Oligo SEQ ID NO: | VIABILITY | | RECOVERY | |
|---|---|---|---|---|
| | AVE. | SD | AVE. | SD |
| NONE | 75.0% | 7.2% | 100.0% | 0.0% |
| 49 | 85.5% | 3.6% | 104.8% | 12.3% |
| 50 | 86.3% | 3.3% | 113.4% | 8.3% |
| 51 | 83.1% | 8.3% | 95.4% | 48.8% |
| 39 | 81.9% | 3.3% | 89.9% | 8.5% |
| 52 | 86.6% | 4.3% | 90.3% | 10.0% |
| 53 | 85.6% | 1.2% | 119.3% | 5.7% |
| 40 | 86.0% | 1.6% | 120.8% | 10.0% |
| 54 | 85.0% | 9.1% | 93.4% | 29.7% |
| 55 | 86.7% | 0.4% | 89.0% | 1.3% |
| 41 | 85.1% | 0.9% | 83.7% | 5.0% |
| 56 | 88.1% | 4.8% | 84.4% | 16.9% |
| 57 | 83.6% | 4.8% | 94.8% | 25.6% |
| 31 | 87.3% | 2.4% | 90.9% | 7.4% |
| 58 | 90.5% | 4.5% | 82.3% | 2.4% |
| 59 | 86.1% | 4.0% | 74.9% | 1.0% |
| 60 | 88.5% | 2.5% | 79.8% | 0.1% |
| 61 | 89.8% | 2.6% | 108.5% | 14.3% |
| 32 | 87.7% | 0.6% | 77.8% | 26.7% |
| 62 | 85.5% | 0.4% | 89.0% | 20.4% |
| 63 | 90.5% | 0.2% | 90.1% | 4.8% |
| 64 | 86.9% | 0.0% | 95.4% | 28.8% |

Experimental

Compounds. Phosphorothioate antisense oligonucleotides were synthesized and HPLC purified by Integrated DNA Technologies, Inc. (Coralville, Iowa).

Electroporation. Electroporation of SaI/CIITA cells at 200 V and 1200 $\mu$F, with individual oligonucleotides (50 $\mu$M), was performed as described in Example 2. Cells were incubated for 24 hours before quantifying MHC class II and Ii proteins.

Assay for membrane bound MHC class II protein. Cells was incubated with 20 $\mu$g/ml rat anti-mouse I-E$^k$ monoclonal antibody M5/114.15.2 (American Type Culture Collection, Rockville, Md.) on ice for 60 minutes, washed twice with Hank's balanced salts solution, followed by 1:100 dilution of a FITC-labeled F(ab')$_2$ of goat anti-rat IgG (Southern Biotechnology Associates, Inc., Birmingham, Ala.) for 30 minutes at room temperature. Cells were washed three times with Hank's solution and fixed with 2% formalin for 15 minutes on ice. FACS analysis was used to determine the percentage of fluorescent cells indicating presence of MHC class II protein.

Assay for intracellular Ii protein. Cells were fixed with 2% formalin, washed once with 1 M glycine, and twice with Hanks' buffer salts solution containing 20 mM HEPES and 0.2% saponin. Cells were stained first with rat anti-mouse Ii monoclonal antibody In.1 (Koch, N. et al., Nature 299: 644–645, 1982) as a hybridoma culture supernate, washed and then incubated with FITC-labeled F(ab')2 of goat anti-rat IgG. Cells were washed and fixed again, as above. The immunofluorescence of individual cells was determined with a FACS.

EXAMPLE 4

Relative Potencies of Various Backbone Modifications in Inhibition of Ii Protein Expression In this study, the most active antisense sequence identified in Example 3, SEQ ID NO:54 was used to compare relative potencies of various backbone modifications in inhibition of Ii protein expression. Four backbone modification of the same sequence (SEQ ID NO:54) were prepared (Table 7): (1) phosphorothioate oligo, (2) mixed backbone of phosphodiester in the middle with 2' methyloxyl modified phosphorothioate at the 5' and 3' end oligo, (3) mixed backbone of phosphorothioate in the middle with 2' methyloxyl modified phosphorothioate at the 5' and 3' end oligo, and (4) 2' methyloxyl modified phosphodiester oligo. 10 and 50 mM each of the oligonucleotides were electroporated into SaI/CIITA sarcoma cells which were then cultured for 24 or 48 hours. Levels of inhibition in Ii protein expression as well as the effect of the oligonucleotides on MHC class II protein expression was quantified by FACS analysis. As shown in Table 8, Oligonucleotide oligonucleotide 54 and oligonucleotide 66, each having a phosphorothioate backbone, gave rise to comparable inhibition of Ii protein without affecting MHC class II expression. The other two oligonucleotides with a phosphodiester backbone showed less inhibition of Ii expression. Cell viability was tested in the presence or absence of oligonucleotides, showing that all oligonucleotides had minimal cytotoxic effects. Since synthesis of phosphorothioate oligonucleotides produces higher yield, quicker turnover, at lower expense, copolymers with this type of backbone were used in all subsequent experiments.

TABLE 7

Sequences of oligonucleotides with different backbone structures.

| OLIGO NO: | SEQUENCE AND COMPOSITION |
|---|---|
| 54 (SEQ ID NO:54) | 5' TsGsGs TsCsAs TsCsCs AsTsGs GsCsTs CsTsA 3'<br>All phosphorothioate. |
| 65 (SEQ ID NO:54) | 5' TsGsGs TsCA TCC ATG GCsTs CsTsA 3'<br>    \| \| \| \|          \| \|  \| \|<br>     2' OMe          2' OMe<br>First and last 4 are phosphorothioate and 2' methyloxyl. The middle 9 bases are phosphodiester. |
| 66 | 5' TsGsGs TsCsAs TsCsCs AsTsGs GsCsTs CsTsA 3'<br>    \| \| \| \|                         \| \| \| \|<br>    2'OMe                        2' OMe<br>All phosphorothioate. First and last 4 are 2' methyloxyl. |
| 67 (SEQ ID NO:54) | 5' TGG TCA TCC ATG GCT CTA 3'<br>    \|\|\| \|\|\| \|\|\| \|\|\| \|\|\| \|\|\|<br>2'OMe 2'OMe 2'OMe 2'OMe<br>All phosphodiester and 2' methyloxyl |

TABLE 8

Inhibition of Ii expression by antisense oligonucleotides with differing backbone structures.

| OLIGO | | Ii NEGATIVE CELLS | | I-E NEGATIVE CELLS | | VIABILITY | |
|---|---|---|---|---|---|---|---|
| NO: | CONC. | 24 HOURS | 48 HOURS | 24 HOURS | 48 HOURS | 24 HOURS | 48 HOURS |
| NONE | | 8.33% | 25.40% | 4.06% | 6.46% | 64.02% | 45.50% |
| 54 | 10 mM | 20.68% | 63.06% | 4.76% | 5.74% | 66.67% | 38.10% |
|  | 50 mM | 32.36% | 60.16% | 4.36% | 6.14% | 62.35% | 44.90% |
| 65 | 10 mM | 10.56% | 45.30% | 3.72% | 5.58% | 63.86% | 49.09% |
|  | 50 mM | 18.84% | 46.88% | 3.48% | 6.96% | 62.79% | 48.57% |
| 66 | 10 mM | 20.66% | 62.24% | 4.10% | 6.26% | 72.13% | 44.83% |
|  | 50 mM | 29.78% | 62.82% | 4.30% | 7.46% | 69.12% | 47.73% |
| 67 | 10 mM | 7.84% | 46.90% | 3.90% | 6.18% | 61.90% | 48.57% |
|  | 50 mM | 8.79% | 41.24% | 4.36% | 6.68% | 66.20% | 47.06% |

Experimental

Compounds. Antisense oligonucleotides, as listed in Table 7, were synthesized and HPLC-purified by Integrated DNA Technologies, Inc. (Coralville, Iowa). Electroporation, cell culture, and FACS assay for intracellular Ii and surface I-E expression are the same as in Example 3.

EXAMPLE 5
Inhibition of Ii Protein Expression by Ii Reverse Gene Constructs For these experiments, SaI sarcoma cells were first transfected with the gene for the CIITA transacting factor which up-regulates expression of MHC Class II molecules (Armstrong et al., *Proc. Natl. Acad. Sci. USA* 94: 6886 (1997)) to produce SaI/CIITA cells. Several Ii reverse gene constructs were made by inserting the DNA sequences listed in Table 9, which correspond to Ii mRNA sequences (coresponding sequence numbers are indicated), into expression vectors. The reverse gene constructs were then transfected into SaI/CIITA cells. Cells which had received the expression vectors were selected by growth in hygromycin containing medium. These cells were stained intracellularly for expression of Ii using the monoclonal antibody In.1. Ii expression of these cells was then quantitated by FACS analysis.

Inhibition of Ii protein expression (up to 60% of cells) was observed in transfectants by some of the mIi reverse gene constructs. The data summarized in Table 10 indicate that the reverse gene constructs made from the sequences listed in SEQ ID NO:68, SEQ ID NO:71, SEQ ID NO:72, SEQ ID NO:75, SEQ ID NO:77, SEQ ID NO:78, and SEQ ID NO:79, significantly suppressed Ii protein expression in an appreciable fraction of the treated cells.

Table 9. Sequences of Reverse Gene Constructs

SEQ ID NO:68
−26TGTG GGAAAAACTA GAGGCTAGAG CCATG-GATGACCAACGCGAC CTCATCT CTAACCATGAA-CAGTTGCCC ATA CTGGGCAACC GCCCTA-GAGAGCCAGAAAG77

SEQ ID NO:69
32ATACTGGGCAACC GCCCTAGAGAGCCAGAAAG-GTGCAGCCGTG GAGCTCTGTA CACCGGT-GTCTCTGTCCTGG TGG CTCTGCT CTTGGCTG136

SEQ ID NO:70
234ACCT GTGAGCCAGA TGCGGATGGCTACTCCCT-TGCTGATGCGTCCAATGT CCATG GATAACATG CTCCTTGGGCCTGTGAAGAA CGTTACCAAG TACGGCAACA TGACCCAGGA CCATGTGATG CATCTG CTCA368

SEQ ID NO:71
314 AAGAA CGTTACCAAG TACGGCAACATGAC-CCAGGA CCATGTGATG CATCTG CTCA CGAG-GTCTGG ACCCCTGGAGTACCCGCAGC TGAAGGGGAC CTTCCCAGAG AATCTGAAGC ATCTTAAGAACTCCATGGAT GGCGTGAACT458

SEQ ID NO:72
−92 GGGTCCCAGA CACACAGCAG CAGCAGCAGC AGCAGCAGCA GCAACAGCAG CAGCAGCAGC AGCGCC TGTG GGAAAAACTA GAGGCTAGAG CCATGGATGA CCAACGCGACCTCATCTCTAAC-CATGAACAGTTGCCCATACTGGGCAACCGCCC TAGAGAGCCAGAAAG77

SEQ ID NO:73
−2 CCATGGATGACCAACGCGAC CTCATCTCTA ACCATGAACA GTTGCCC ATA CTGGGCAACC GCCCTAGAGAGCCAGAAAG gtatgtgtgaataccagca-gagagcccttaccctcgg aggacacagaatgcaggcctggggagggacacagagctctgttg81 (Intron 1)

SEQ ID NO:74
78GTGCAGCCGTG GAGCTCTGTA CACCGGTGTC TCTGTCCTGG TGG CTCTGCTCT TGGCTGGGCAG-GCCACCACTGCTTACTT CCTGTACCAG CAA-CAGGGCCGCCTAGAC AAGCTGACCATCACCTC-CCAGAACCTGCAACTGGAGAGCCTTCGCATGAA-GCTTCCG AAATgtgcgtgctccacctgtccctcac-ctcacagacatcatttctccatttagcccctc ccgatctgcct67(Intron 2)

SEQ ID NO:75
−92 GGGTCCCAGA CACACAGCAG CAGCAGCAG-CAGCAGCAGCAGCAACAGCAGCAG CAGCAG-CAGCGCC TGTG GGAAAAACTAGAGGCTAGAG CCATGGATGACCAACGC15

SEQ ID NO:76
last 13(intron 1)tccgtcccaacagATACTGGGCAACC GCCCTAGAGAGCCAGAAAGGT GCAG CCGTG GAG CTCTGTA CACCGGTGTCTCTGTCCTGG TGG CTCTGCT CTTGGCTG136

SEQ ID NO:77
−92 GGGTCCCAGA CACACAGCAG CAGCAGCAGC AGCAGCAGCA GCAACAGCAG CA GCAGCAGC AGCGCC TGTG GGAAAAACTA GAGGCTAGAG CCATGGATGACCAACG CGACCTCATCTCTAAC-CATGAACAGTTGCCCATACTGGGCAAC-CGCCCTAGAGAGCC AGAAAGGTGCAGCCGTG GAGCTCTGTA97

SEQ ID NO:78
−50AACAGCAGCAGCAGCAGCAGCGCCTGTGGGA-AAAACTAGAGGCTAGAGCCATGG ATGACCAACG CGACCTCATCTCTAACCATGAACAGTTGCCCAT-ACTGGGCAACCGCC AGAGCCAGAAAGGTG-CAGCCGTG GAGCTCTGTA97

SEQ ID NO:79
−26TGTGGGAAAAACTAGAGGCTAGAGCCATGGAT-GACCAACG CGACCTCATCTCTA ACCATGAA-CAGTTGCCCATACTGGGCAACCGCC CTA-GAGAGCCAGAAAGGTGCAGC CGTGGAGCTCT-GTA97

TABLE 10

Activities of reverse gene constructs

| SEQ ID NO: | RGC Constructs | Position in Ii Gene | * Ii Inhibition |
|---|---|---|---|
| 68 | pcDNA3.1(+)/mIi (−26, 77) | 5' UT to 1st exon | (+) |
| 69 | pcDNA3.1(+)/mIi (32, 136) | 1st and 2nd exon | (−) |
| 70 | pcDNA3.1(+)/mIi(234, 368) | 3rd and 4th exon | (−) |
| 71 | pcDNA3.1(+)/mIi(314, 458) | 4th and 5th exon | (+) |
| 72 | pcDNA3.1(+)/mIi(−92, 77) | 5' UT to 1st exon | (+) |
| 73 | pcDNA3.1(+)/mIi(−2, 1in81) | 1st exon to 1st intron | (−) |
| 74 | pcDNA3.1(+)/mIi(78, 2in67) | 2nd exon to 2nd intron | (−) |
| 75 | pcDNA3.1(+)/mIi(−92, 15) | 5' UT and AUG | (+) |
| 76 | pcDNA3.1(+)/mIi(1in13, 136) | 2nd intron to 3rd exon | (−) |
| 77 | RSV.5 / mIi (−92, 97) | 5' UT to 1st exon | (+) |
| 78 | RSV.5 / mIi (−50, 97) | 5' UT to 1st exon | (+) |
| 79 | RSV.5 / Ii(−26, 97) | 5' UT to 1st exon | (+) |

* Ii inhibition (up to about 60%) was observed (+) in screening of SaI/CIITA stable transfectants with these constructs.

Experimental

Generation of reverse gene constructs. The various Ii reverse gene constructs were made from one of two plasmids. Constructs made from pcDNA3.1(+) (Invitrogen, Carlsbad, Calif.) utilize the cytomegalovirus promoter to drive gene expression. Constructs made from RSV.5 utilize the rouse sarcoma virus promoter (Long et al., *Human Immunology* 31: 229–235 (1991)). Both plasmids contained the hygromycin resistance gene, which was used for selection of transfected cells. The mIi reverse gene fragments were generated by the polymerase chain reaction (PCR). The PCR fragments were digested with Nhe1 and Apa1, and then were cloned into pcDNA3.1(+) digested with same endonucleases. The insertion of mIi reverse gene fragments was confirmed by Nhe1 and Apa1 digestion. The PCR fragments were digested with Sal 1 and BamH1 and then were cloned into RSV.5 plasmid which was digested with the same endonucleases. All the mIi fragments were confirmed by sequencing.

Cells. SaI/CIITA cells, the gift of Dr. Ostrand-Rosenberg, the University of Maryland, Baltimore, Md., were cultured in IMDM (JRH Biosciences, Lenexa, Kans.), containing 5% FCS (FetalClone I, HyClone Laboratories, Logan, Utah).

Transfection. SaI/CIITA cells were transfected with mIi reverse gene constructs using lipofectin (GIBCO BRL) according to the manufacturer's instruction. Briefly, 10 μl of lipofectin and 3–5 mg of plasmid DNA were gently mixed with 100 μl of Opt. MEM I (GIBCO BRL), separately. The reactions were incubated at room temperature for 40 minutes. The two reactions were gently mixed together and incubated at room temperature for another 15 minutes. Meanwhile, $10^5$ SaI/CIITA cells were washed with Opt. MEM I and resuspended into 800 μl of Opt. MEM I. The liposome/DNA reaction was gently dropped into the SaI/CIITA cells and then the cells were incubated at 37° C. for 12–24 hours. The transfection medium was replace with 2 ml of culture medium and the cells were incubated for 24–48 hours before 800 units of hygromycin B (ICN Pharmaceuticals, Inc., Costa Mesa, Calif.) was added to select for transfected cells in 96-well plates.

FACS analysis. The hygromycin resistant cells were stained intracellularly (see Examples 3 and 4 for detailed procedures) for the expression of Ii with monoclonal antibody, In.1. The stained cells were analyzed by FACS.

EXAMPLE 6
Protection Against Tumor Challenge with Ii Protein-suppressed and Fixed Vaccine Cells Experiments were performed to explore the use of Ii protein-suppressed tumor cells as tumor cell vaccines to protect a host from challenge with a parental tumor. For these experiments, SaI sarcoma cells were first transfected with the gene for the CIITA transacting factor which up-regulates expression of MHC Class II molecules (Armstrong et al., *Proc. Natl. Acad. Sci. USA* 94: 6886 (1997)) to produce SaI/CIITA cells. The transfected cells express both MHC class I and MHC class II molecules. Without transfection of the CIITA gene, the SaI cells express only MHC class I molecules. SaI/CIITA cells also express significant amounts of the Ii protein, along with the MHC class II molecules. Coexpression of Ii protein with MHC class II molecules occurs because the CIITA transacting factor also acts on genetic regulatory units upstream from (and within the first intron of) the structural gene for Ii protein (Zhu and Jones, *Molecular and Cellular Biology* 10: 3906 (1990); Moore et al., *J. Immunol.* 161: 1844 (1998)).

The SaI/CIITA cells (expressing MHC Class I, MHC Class II molecules and the Ii protein) were treated with an antisense oligonucleotide directed to Ii mRNA (SEQ.ID.NO.:54) in order to suppress expression of the Ii protein. The degree of suppression of the Ii protein in the SaI/CIITA cells, and the lack of suppression of MHC Class II molecules was measured by methods presented above in Example 3. The antisense oligonucleotide compound SEQ.ID.NO.:54 profoundly suppressed Ii protein in about 35 percent of the SaI/CIITA cells, without significant effect upon the level of expression of MHC Class II molecules. To prevent replication in the inoculated host, the vaccine cells were fixed with formaldehyde.

Mice which had received the Ii suppressed vaccine cells were divide into three subgroups, and each subgroup was challenged with SaI tumors at either $2.5 \times 10^5$ cells/mouse, $7.5 \times 10^5$ cells/mouse, and $20 \times 10^5$ cells/mouse. Control mice which had been treated with fixed SaI/CIITA cells which had not been treated with a copolymer to suppress Ii, were also challenged with the above concentrations of tumor cells. The incidence of tumors in each of the 6 subgroups of mice is presented in Table 11. On day 13, all control mice (C) with ascites tumor, had 1.5–2.5 ml ascites and were terminated. Among the mice which had received CIITA gene-transfected vaccine cells (AS mice), one mouse in the $2.5 \times 10^5$ cells/mouse group and one mouse in the $7.5 \times 10^5$ cells/mouse group, were terminated with 1.5–2.5 ml ascites. None of the mice in the $20 \times 10^5$ cells/mouse group had developed tumors at 61 days.

These observations demonstrate that vaccination of mice with tumor cells expressing MHC Class II molecules, but little or no Ii protein, leads to protective tumor immunity. Since that protection is against parental SaI cells which express MHC Class I, but not MHC class II molecules, immunity is mediated by helper T cells which are restricted by MHC Class II molecules, and is required for development of the final, effector, killer T cell response. That is, since these vaccine cells induce protection against parental SaI cells which are MHC Class I-positive but MHC class II- and Ii protein-negative, protection is mediated by two classes of T cells. First, helper T cells are stimulated by antigenic determinants presented by the MHC class II molecules without the immunoregulatory Ii protein. Second killer T cells, which are restricted by MHC class I molecules, were stimulated to expand and activity by actions of the helper T cells.

TABLE 11

Tumor incidence after challenge with SaI tumors, in mice vaccinated withfixed, SaI/CIITA cells, which had not been or had been treated with compound SEQ. ID. NO.:54.

| DAYS | $2.5 \times 10^5$ | | $7.5 \times 10^5$ | | $20 \times 10^5$ | |
|---|---|---|---|---|---|---|
| | C | AS | C | AS | C | AS |
| 9 | 0/5 | 0/5 | 0/5 | 0/5 | 0/5 | 0/5 |
| 11 | 2/5 | 0/5 | 4/5 | 0/5 | 5/5 | 0/5 |
| 13 | 2/5 | 0/5 | 4/5 | 0/5 | 5/5 | 0/5 |
| 15 | 2/5 | 0/5 | 4/5 | 1/5 | 5/5 | 0/5 |
| 17 | 2/5 | 0/5 | 4/5 | 1/5 | 5/5 | 0/5 |
| 19 | 2/5 | 1/5 | 4/5 | 1/5 | 5/5 | 0/5 |
| 21 | 2/5 | 1/5 | 4/5 | 1/5 | 5/5 | 0/5 |
| 31 | 2/5 | 1/5 | 4/5 | 1/5 | 5/5 | 0/5 |
| 41 | 2/5 | 1/5 | 4/5 | 1/5 | 5/5 | 0/5 |
| 61 | 2/5 | 1/5 | 4/5 | 1/5 | 5/5 | 0/5 |

The incidence of tumor ascites with a volume equal to or greater than 1.5 ml was scored in mice vaccinated with CIITA gene-transfected tumor cells which were treated with SEQ.ID.NO.:54 ("AS" for antisense, subgroups), or were not treated ("C" for control, subgroups).

Experimental

Transfection. The CIITA-gene transfected SaI cells were incubated at $2 \times 10^6$ cells/ml with 50 μM compound SEQ.ID.NO.:54 and subjected to electroporation at 200 V, 1200 μfd in a BTX ECM 600 electroporation system. The cells were subsequently cultured in IMDM medium with 5% fetal calf serum for 20 hours, prior to immunofluorescence analysis for protein expression and fixation.

Fixation. Cells were fixed with 0.15% formaldehyde in phosphate-buffer saline solution, pH 7.2, for 15 minutes at room temperature, and washed.

Inoculation. Vaccine cells were injected intraperitoneally into 15 mice at $2.5 \times 10^5$ cells/mouse. A parallel group of fifteen mice were injected with SaI/CIITA cells which had not been treated with the SEQ.ID.NO.:54 copolymer.

Tumor challenge. After 27 days, mice in three subgroups (5 mice per subgroup), of the mice which had been vaccinated with SaI/CIITA cells treated with SEQ.ID.NO:54, were challenged with SaI parental cells at three doses: $2.5 \times 10^5$ cells, $7.5 \times 10^5$ cells and $20 \times 10^5$ cells, respectively. In parallel, three subgroups of mice vaccinated with fixed, SaI/CIITA cells which had not been treated with SEQ.ID.NO.:54, were challenged with SaI parental cells at the same three doses, respectively. These challenge doses had been determined in a previous experiment to titrate a cell dose/tumor incidence curve.

EXAMPLE 7
Protection Against Tumor Challenge with Ii Protein-suppressed and Irradiated, Vaccine Cells The experiments of this Example paralleled in strategy those of Example 6, excepting principally two elements. First, the MHC Class II molecules and the Ii protein were induced in SaI cells after transfection of the gene for interferon gamma, rather than after transfection of the gene for CIITA. Second, viability of the vaccine cells was maintained by irradiation, while the malignant potential (ability to replicate) was destroyed.

There are several practical scientific and economic reasons to prefer to induce MHC Class II molecules through the action of interferon gamma, rather than CIITA. For example, the action of interferon gamma might induce additional functions needed for optimal processing and presentation of tumor-related antigenic determinants. In addition, permitting the tumor cells to continue to live (without replicating) for some time after introduction into the host, confers favorable properties, for example, in terms of continuing exposure to antigenic determinants, cumulative antigenic dose, duration of interaction with multiple accessory and effector cells of the immune system.

For these experiments, the SaI sarcoma was transfected by electroporation with the interferon gamma gene (Chen and Ananthaswamy, *J. Immunol.* 151: 244–255 (1993)) inserted in the pGKNeo plasmid. The initial selection was in 800 μg/ml G418 and maintenance was in 400 ug/ml G418. Interferon gamma producing cells were selected by culturing at limiting dilution, and expansion of clonal populations which were identified by surface expression of MHC Class II molecules with the 5/114.15.2 monoclonal antibody from ATCC hybridoma T1B120 by visual immunofluorescence.

Two classes of vaccine protecting cell populations were prepared: 1) cells transfected with copolymer SEQ.ID.NO.:54 to suppresses Ii protein expression, and 2) cells which were not transfected. CIITA gene-transfected SaI cells were incubated at $2 \times 10^6$ cells/ml with 50 μM copolymer SEQ.ID.NO.:54 and electroporated at 200 V, 1200 μfd in a BTX ECM 600 electroporation system. The cells were subsequently cultured in IMDM medium with 5% fetal calf serum for 24 or 48 hours, prior to immunofluorescence analysis of protein expression or preparation of the vaccine. Prior to vaccination, the cells were subjected to 3,500 rads irradiation in a Cesium-irradiator.

Mice were injected on days 1, 2, and 3 with $2 \times 10^6$ cells/dose of three types of irradiated, interferon [IFN] gamma gene-transfected cells: 1) IFN-gamma gene-transfected cells ("C" in Table 12), 2) IFN-gamma gene-transfected cells cultured for 24 hours after treatment with compound SEQ.ID.NO.:54, so that Ii protein was suppressed in about 34% of cells, without effect on MHC class II molecules ("AS-24" in table 12), and 3) IFN-gamma gene-transfected cells cultured for 48 hours after treatment with compound SEQ.ID.NO.:54, so that Ii protein was suppressed in about 45% of cells, without effect on MHC class II molecules ("AS-48" in Table 12).

After 24 days subgroups of mice in each vaccination group, were challenged with one of three levels of SaI sarcoma cells: $2 \times 10^6$, $5 \times 10^6$, or $12.5 \times 10^6$ cells (Table 12). 0/4, 2/4, and 4/4 of the control subgroups developed 2–3 ml ascites on day 11 and were terminated on day 13. For AS-24 and AS-48 mice, reported endpoints in Table 12 represent date of termination of mice with greater than 2 ml ascites. On day 31 surviving mice had no evidence of malignancy.

These results demonstrate effective tumor protection against a MHC class I-positive, MHC class II-negative, 'parental' cell, by vaccination with an 'engineered' derivative-tumor cell in which Ii-protein is suppressed, and MHC class II molecules are expressed. This indicates that presentation of an expanded repertoire of 'helper' determinants by MHC class II molecules in the absence of Ii protein, leads to enhancement of the anti-tumor response.

TABLE 12

Tumor incidence after challenge with SaI tumors, in mice vaccinated with fixed, interferon gamma gene-transfected SaI-cells, without or with treatment with compound SEQ. ID. NO.: 54.

| | $2 \times 10^6$ | | | $5 \times 10^6$ | | | $12.5 \times 10^6$ | | |
|---|---|---|---|---|---|---|---|---|---|
| DAYS | C | AS-24 | AS-48 | C | AS-24 | AS-48 | C | AS-24 | AS-48 |
| 9 | 0/4 | 0/4 | 0/5 | 0/4 | 0/5 | 0/5 | 0/4 | 0/5 | 0/5 |
| 11 | 0/4 | 0/4 | 0/5 | 2/4 | 0/5 | 0/5 | 4/4 | 0/5 | 0/5 |
| 13 | 0/4 | 0/4 | 0/5 | 2/4 | 0/5 | 0/5 | 4/4 | 0/5 | 0/5 |
| 15 | 0/4 | 0/4 | 0/5 | 2/4 | 0/5 | 0/5 | 4/4 | 0/5 | 0/5 |
| 17 | 0/4 | 0/4 | 0/5 | 2/4 | 0/5 | 0/5 | 4/4 | 0/5 | 0/5 |
| 19 | 0/4 | 0/4 | 0/5 | 3/4 | 0/5 | 0/5 | 4/4 | 0/5 | 0/5 |
| 21 | 0/4 | 1/4 | 0/5 | 3/4 | 3/5 | 3/5 | 4/4 | 1/5 | 2/5 |
| 24 | 0/4 | 1/4 | 0/5 | 3/4 | 3/5 | 4/5 | 4/4 | 1/5 | 2/5 |

TABLE 12-continued

Tumor incidence after challenge with SaI tumors,
in mice vaccinated with fixed, interferon gamma gene-transfected SaI-cells,
without or with treatment with compound SEQ. ID. NO.: 54.

| | $2 \times 10^6$ | | | $5 \times 10^6$ | | | $12.5 \times 10^6$ | | |
| --- | --- | --- | --- | --- | --- | --- | --- | --- | --- |
| DAYS | C | AS-24 | AS-48 | C | AS-24 | AS-48 | C | AS-24 | AS-48 |
| 29 | 0/4 | 1/4 | 0/5 | 3/4 | 3/5 | 4/5 | 4/4 | 1/5 | 2/5 |
| 31 | 0/4 | 1/4 | 0/5 | 3/4 | 3/5 | 4/5 | 4/4 | 1/5 | 2/5 |

What is claimed is:

1. An MHC class II-positive antigen presenting cell which does not contain an exogenous construct encoding mammalian B7 molecule, and which contains a specific regulator of Ii protein expression or immunoregulatory function, the oligonucleotide CTCGGTACCTACTGG being specifically excluded, the specific regulator consisting essentially of a copolymer of from 10 to 50 nucleotide bases, the copolymer being characterized by the ability to hybridize specifically to a target region of the RNA molecule encoding mammalian Ii protein under physiological conditions, wherein the specific regulator is characterized by the ability to inhibit Ii expression.

2. The MHC Class II-positive antigen presenting cell of claim 1 wherein the nucleotide bases are joined to a backbone which includes moieties selected from the group consisting of phosphoramidate, phosphotriester, 2'-deoxyribose, 2'-O-alkyl ribose, 2'-O-alkenyl ribose, 2'-O-substituted alkyl ribose, morpholine, an amide linkage, and homologs.

3. The MHC Class II-positive antigen presenting cell of claim 2 wherein the nucleotide bases are selected from the group consisting of adenine, cytosine, guanine, thymine, uracil, 2,6-diaminopurine, 5-propynyl uracil, 5-propynyl cytosine and homologs.

4. The MHC Class II-positive antigen presenting cell of claim 3 wherein the specific regulator comprises a nucleotide base sequence complementary to the translation initiation site of the RNA molecule encoding mammalian Ii protein.

5. The MHC Class II-positive antigen presenting cell of claim 4 wherein the specific regulator comprises the nucleotide base sequence of SEQ ID NO: 54.

6. The MHC Class II-positive antigen presenting cell of claim 4 wherein the specific regulator comprises the nucleotide base sequence of SEQ ID NO: 53.

7. The MHC Class II-positive antigen presenting cell of claim 4 wherein the specific regulator comprises the nucleotide base sequence of SEQ ID NO: 52.

8. The MHC Class II-positive antigen presenting cell of claim 4 wherein the specific regulator comprises the nucleotide base sequence of SEQ ID NO: 40.

9. The MHC Class II-positive antigen presenting cell of claim 4 wherein the specific regulator comprises the nucleotide base sequence of SEQ ID NO: 55.

10. The MHC Class II-positive antigen presenting cell of claim 3 wherein the specific regulator comprises a nucleotide base sequence which is complementary to a portion of exons bonding a splice site of the RNA molecule.

11. The MHC Class II-positive antigen presenting cell of claim 10 wherein the specific regulator comprises the nucleotide base sequence of SEQ ID NO: 32.

12. The MHC Class II-positive antigen presenting cell of claim 10 wherein the specific regulator comprises the nucleotide base sequence of SEQ ID NO: 62.

13. The MHC Class II-positive antigen presenting cell of claim 3 wherein the specific regulator inhibits intron splicing of the RNA molecule.

14. The MHC Class II-positive antigen presenting cell of claim 3 wherein the specific regulator is complementary to a portion of the 3' end of the first exon and a portion of the 5' end of the first intron of the RNA molecule.

15. The MHC Class II-positive antigen presenting cell of claim 3 wherein the specific regulator is complementary to a region 3' of the termination codon of the RNA molecule.

16. The MHC Class II-positive antigen presenting cell of claim 15 wherein the specific regulator comprises the nucleotide base sequence of SEQ ID NO: 64.

17. The MHC Class II-positive antigen presenting cell of claim 3 wherein the specific regulator is complementary to a region 5' of the initiation codon of the RNA molecule.

18. The MHC Class II-positive antigen presenting cell of claim 17 wherein the specific regulator comprises the nucleotide base sequence of SEQ ID NO: 48.

19. The MHC Class II-positive antigen presenting cell of claim 3 wherein the specific regulator is complementary to a region encoding the CLIP peptides.

20. The MHC Class II-positive antigen presenting cell of claim 19 wherein the specific regulator comprises the nucleotide base sequence of SEQ ID NO: 11.

21. The MHC Class II-positive antigen presenting cell of claim 3 wherein the specific regulator is conjugated at terminal or internal sites to one or more chemical groups which cross link the specific regulator to the hybridized RNA molecule.

22. The MHC Class II-positive antigen presenting cell of claim 21 wherein the chemical group is an alkylating group.

23. The MHC Class II-positive antigen presenting cell of claim 3 wherein the specific regulator is conjugated to a chemical group which catalyzes cleavage of the hybridized RNA molecule.

24. The MHC Class II-positive antigen presenting cell of claim 23 wherein the chemical group is a chelating agent.

25. The MHC Class II-positive antigen presenting cell of claim 3 wherein the specific regulator is a ribozyme designed to cleave the RNA molecule.

26. The MHC Class II-positive antigen presenting cell of claim 3 wherein the specific regulator is conjugated to a chemical group which intercalates into the nucleotide bases of the RNA molecule encoding mammalian Ii protein to stabilize hybridization.

27. The MHC Class II-positive antigen presenting cell of claim 3 wherein the specific regulator is conjugated to a chemical moiety which enhances cellular uptake.

28. The MHC Class II-positive antigen presenting cell of claim 3 wherein the specific regulator is conjugated to a chemical moiety which directs uptake by a specific cell type.

29. The MHC Class II-positive antigen presenting cell of claim 3 wherein the specific regulator is conjugated to a chemical moiety which improves the pharmacological properties or toxicity profile.

30. The MHC Class II-positive antigen presenting cell of claim 1 wherein the specific regulator is a cDNA molecule.

31. The MHC Class II-positive antigen presenting cell of claim 30 wherein the specific regulator comprises the nucleotide base sequence of SEQ ID: 68.

32. The MHC Class II-positive antigen presenting cell of claim 30 wherein the specific regulator comprises the nucleotide base sequence of SEQ ID: 71.

33. The MHC Class II-positive antigen presenting cell of claim 30 wherein the specific regulator comprises the nucleotide base sequence of SEQ ID: 72.

34. The MHC Class II-positive antigen presenting cell of claim 30 wherein the specific regulator comprises the nucleotide base sequence of SEQ ID: 75.

35. The MHC Class II-positive antigen presenting cell of claim 30 wherein the specific regulator comprises the nucleotide base sequence of SEQ ID: 77.

36. The MHC Class II-positive antigen presenting cell of claim 30 wherein the specific regulator comprises the nucleotide base sequence of SEQ ID: 78.

37. The MHC Class II-positive antigen presenting cell of claim 30 wherein the specific regulator comprises the nucleotide base sequence of SEQ ID: 79.

38. The MHC Class II-positive antigen presenting cell of claim 1 wherein the specific regulator is expressed from a viral expression vector.

39. The MHC Class II-positive antigen presenting cell of claim 38 wherein the viral expression vector is characterized by the ability to enhance transfection into mammalian cells.

* * * * *

UNITED STATES PATENT AND TRADEMARK OFFICE
CERTIFICATE OF CORRECTION

PATENT NO. : 6,368,855 B1
DATED : April 9, 2000
INVENTOR(S) : Xu et al.

It is certified that error appears in the above-identified patent and that said Letters Patent is hereby corrected as shown below:

Column 68,
Line 6, delete "bonding" and substitute therefor -- bounding --.

Column 69,
Line 11, delete "claim 3" and substitute therefor -- claim 13 --.

Signed and Sealed this

Second Day of July, 2002

Attest:

Attesting Officer

JAMES E. ROGAN
Director of the United States Patent and Trademark Office

SEQUENCE LISTING

<160> NUMBER OF SEQ ID NOS: 79

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the Ii gene.

<400> SEQUENCE: 1
ctcggtacct actgg                                                        15

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 2
atccatggct ctagcctc                                                     18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 3
tctagcctct agtttttc                                                     18

<210> SEQ ID NO 4
<211> LENGTH:
<212> TYPE:
<213> ORGANISM:

<400> SEQUENCE: 4

000

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: antisense oligonucleotide corresponding to a specific region
        of the mouse Ii gene.

<400> SEQUENCE: 5
catgttatcc atggacat                                                     18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: antisense
        oligonucleotide corresponding to a specific region
        of the mouse Ii gene.

<400> SEQUENCE: 6
catggacatt ggacgcat                                                     18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: antisense
        oligonucleotide corresponding to a specific region
        of the mouse Ii gene.

<400> SEQUENCE: 7
tggacgcatc agcaaggg                                                     18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: antisense
        oligonucleotide corresponding to a specific region
        of the mouse Ii gene.

<400> SEQUENCE: 8
cagcaaggga gtagccat                                                     18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: antisense
        oligonucleotide corresponding to a specific region
        of the mouse Ii gene.

<400> SEQUENCE: 9
agtagccatc cgcatctg                                                     18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: antisense
        oligonucleotide corresponding to a specific region
        of the mouse Ii gene.

<400> SEQUENCE: 10
ccgcatctgg ctcacagg                                                     18

<210> SEQ ID NO 11

<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 11
gctcacaggt ttggcaga                                                 18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 12
tttggcagat tcggaag                                                  18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 13
tttcggaagc ttcatgcg                                                 18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 14
cttcatgcga aggctctc                                                 18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 15
aaggctctcc agttgcag                                                 18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 16

```
cagttgcagg ttctggga                                                  18
```

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 17

```
gttctgggag gtgatggt                                                  18
```

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 18

```
ggtgatggtc agcttgtc                                                  18
```

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 19

```
cagcttgtct aggcggcc                                                  18
```

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 20

```
taggcggccc tgttgctg                                                  18
```

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 21

```
ctgttgctgg tacaggaa                                                  18
```

<210> SEQ ID NO 22
<211> LENGTH: 18
<212> TYPE: DNA
<213> ORGANISM: Artificial Sequence
<220> FEATURE:

-continued

```
<223> OTHER INFORMATION: Description of Artificial Sequence: antisense
      oligonucleotide corresponding to a specific region
      of the mouse Ii gene.

<400> SEQUENCE: 22
gtacaggaag taagcagt                                               18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 23
gtaagcagtg gtggcctg                                               18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 24
ggtggcctgc ccagccaa                                               18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 25
cccagccaag agcagagc                                               18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 26
gagcagagcc accaggac                                               18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 27
caccaggaca gagacacc                                               18
```

```
<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 28
agagacaccg gtgtacag                                                    18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 29
ggtgtacaga gctccacg                                                    18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 30
agctccacgg ctgcacct                                                    18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 31
gctgcacctt tctggctc                                                    18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 32
ttctggctct ctagggcg                                                    18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.
```

-continued

```
<400> SEQUENCE: 33
tctagggcgg ttgcccag                                              18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 34
gttgcccagt atgggcaa                                              18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 35
tatgggcaac tgttcatg                                              18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 36
ctgttcatgg ttagagat                                              18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 37
gttagagatg aggtcgcg                                              18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 38
gaggtcgcgt tggtcatc                                              18

<210> SEQ ID NO 39
<211> LENGTH: 18
<212> TYPE: DNA
<213> ORGANISM: Artificial Sequence
```

```
<220> FEATURE:
<223> OTHER INFORMATION: Description of Artificial Sequence: antisense
      oligonucleotide corresponding to a specific region
      of the mouse Ii gene.

<400> SEQUENCE: 39
gcgttggtca tccatggc                                                   18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 40
ttggtcatcc atggctct                                                   18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 41
gtcatccatg gctctagc                                                   18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 42
cacaggcgct gctgctgc                                                   18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 43
atccatggct ctagccct                                                   18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 44
tctagcccta gtttttcc                                                   18
```

```
<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 45
agtttttccc acaggcgc                                                    18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 46
atggatgacc aacgcgac                                                    18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 47
ctagtttttc ccacaggc                                                    18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 48
ctgctgctgt tgctgctg                                                    18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 49
gtcgcgttgg tcatccat                                                    18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.
```

<400> SEQUENCE: 50
tcgcgttggt catccatg          18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 51
cgcgttggtc atccatgg          18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 52
cgttggtcat ccatggct          18

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 53
gttggtcatc catggctc          18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 54
tggtcatcca tggctcta          18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 55
ggtcatccat ggctctag          18

<210> SEQ ID NO 56
<211> LENGTH: 18
<212> TYPE: DNA

```
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 56
cacggctgca cctttctg                                                    18

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 57
cggctgcacc tttctggc                                                    18

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 58
tgcacctttc tggctctc                                                    18

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 59
cacctttctg gctctcta                                                    18

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 60
acctttctgg ctctctag                                                    18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 61
ctttctggct ctctaggg                                                    18
```

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 62
ctggctctct agggcggt                                             18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 63
ggctctctag ggcggttg                                             18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: antisense
      oligonucleotide corresponding to a specific region
      of the mouse Ii gene.

<400> SEQUENCE: 64
gacaagcttg gctgagca                                             18

<210> SEQ ID NO 65
<211> LENGTH:
<212> TYPE:
<213> ORGANISM:

<400> SEQUENCE: 65

000

<210> SEQ ID NO 66
<211> LENGTH:
<212> TYPE:
<213> ORGANISM:

<400> SEQUENCE: 66

000

<210> SEQ ID NO 67
<211> LENGTH:
<212> TYPE:
<213> ORGANISM:

<400> SEQUENCE: 67

000

<210> SEQ ID NO 68
<211> LENGTH: 103
<212> TYPE: DNA
<213> ORGANISM: Artificial Sequence
<220> FEATURE:

```
<223> OTHER INFORMATION: Description of Artificial Sequence: Reverse
      gene construct corresponding to a  specific region of
      the mouse Ii gene.

<400> SEQUENCE: 68
tgtgggaaaa actagaggct agagccatgg atgaccaacg cgacctcatc tctaaccatg      60
aacagttgcc catactgggc aaccgcccta gagagccaga aag                      103

<210> SEQ ID NO 69
<211> LENGTH: 91
<212> TYPE: DNA
<213> ORGANISM: Artificial Sequence
<220> FEATURE:
<223> OTHER INFORMATION: Description of Artificial Sequence: Reverse
      gene construct corresponding to a  specific region of
      the mouse Ii gene.

<400> SEQUENCE: 69
atactgggca accgccctag agagccagaa aggtgcagcc gtggagctct gtacaccggt      60
gtctctgtcc tggtggctct gctcttggct g                                   91

<210> SEQ ID NO 70
<211> LENGTH: 134
<212> TYPE: DNA
<213> ORGANISM: Artificial Sequence
<220> FEATURE:
<223> OTHER INFORMATION: Description of Artificial Sequence: Reverse
      gene construct corresponding to a  specific region of
      the mouse Ii gene.

<400> SEQUENCE: 70
acctgtgagc cagatgcgga tggctactcc cttgctgatg cgtccaatgt ccatggataa      60
catgctcctt gggcctgtga agaacgttac caagtacggc aacatgaccc aggaccatgt    120
gatgcatctg ctca                                                      134

<210> SEQ ID NO 71
<211> LENGTH: 145
<212> TYPE: DNA
<213> ORGANISM: Artificial Sequence
<220> FEATURE:
<223> OTHER INFORMATION: Description of Artificial Sequence: Reverse
      gene construct corresponding to a  specific region of
      the mouse Ii gene.

<400> SEQUENCE: 71
aagaacgtta ccaagtacgg caacatgacc caggaccatg tgatgcatct gctcacgagg      60
tctggacccc tggagtaccc gcagctgaag gggaccttcc cagagaatct gaagcatctt    120
aagaactcca tggatggcgt gaact                                          145

<210> SEQ ID NO 72
<211> LENGTH: 169
<212> TYPE: DNA
<213> ORGANISM: Artificial Sequence
<220> FEATURE:
<223> OTHER INFORMATION: Description of Artificial Sequence: Reverse
      gene construct corresponding to a  specific region of
      the mouse Ii gene.

<400> SEQUENCE: 72
gggtcccaga cacacagcag cagcagcagc agcagcagca gcaacagcag cagcagcagc      60
agcgcctgtg ggaaaaacta gaggctagag ccatggatga ccaacgcgac ctcatctcta    120
accatgaaca gttgcccata ctgggcaacc gccctagaga gccagaaag               169
```

<210> SEQ ID NO 73
<211> LENGTH: 160
<212> TYPE: DNA
<213> ORGANISM: Artificial Sequence
<220> FEATURE:
<223> OTHER INFORMATION: Description of Artificial Sequence: Reverse
      gene construct corresponding to a  specific region of
      the mouse Ii gene.

<400> SEQUENCE: 73
ccatggatga ccaacgcgac ctcatctcta accatgaaca gttgcccata ctgggcaacc      60
gccctagaga gccagaaagg tatgtgtgaa taccagcaga gagcccttac ctctggagga    120
cacagaatgc aggcctgggg agggacacag agctctgttg                          160

<210> SEQ ID NO 74
<211> LENGTH: 237
<212> TYPE: DNA
<213> ORGANISM: Artificial Sequence
<220> FEATURE:
<223> OTHER INFORMATION: Description of Artificial Sequence: Reverse
      gene construct corresponding to a  specific region of
      the mouse Ii gene.

<400> SEQUENCE: 74
gtgcagccgt ggagctctgt acaccggtgt ctctgtcctg gtggctctgc tcttggctgg      60
gcaggccacc actgcttact tcctgtacca gcaacagggc cgcctagaca agctgaccat    120
cacctcccag aacctgcaac tggagagcct tcgcatgaag cttccgaaat gtgcgtgctc    180
cacctgtccc tcacctcaca gacatcattt ctccatttag cccctcccga tctgcct       237

<210> SEQ ID NO 75
<211> LENGTH: 107
<212> TYPE: DNA
<213> ORGANISM: Artificial Sequence
<220> FEATURE:
<223> OTHER INFORMATION: Description of Artificial Sequence: Reverse
      gene construct corresponding to a  specific region of
      the mouse Ii gene.

<400> SEQUENCE: 75
gggtcccaga cacacagcag cagcagcagc agcagcagca gcaacagcag cagcagcagc      60
agcgcctgtg ggaaaaacta gaggctagag ccatggatga ccaacgc                  107

<210> SEQ ID NO 76
<211> LENGTH: 104
<212> TYPE: DNA
<213> ORGANISM: Artificial Sequence
<220> FEATURE:
<223> OTHER INFORMATION: Description of Artificial Sequence: Reverse
      gene construct corresponding to a  specific region of
      the mouse Ii gene.

<400> SEQUENCE: 76
tccgtcccaa cagatactgg gcaaccgccc tagagagcca gaaaggtgca gccgtggagc      60
tctgtacacc ggtgtctctg tcctggtggc tctgctcttg gctg                     104

<210> SEQ ID NO 77
<211> LENGTH: 190
<212> TYPE: DNA
<213> ORGANISM: Artificial Sequence
<220> FEATURE:
<223> OTHER INFORMATION: Description of Artificial Sequence: Reverse
      gene construct corresponding to a  specific region of -continued

```
    the mouse Ii gene.

<400> SEQUENCE: 77
gggtcccaga cacacagcag cagcagcagc agcagcagca gcaacagcag cagcagcagc      60
agcgcctgtg ggaaaaacta gaggctagag ccatggatga ccaacgcgac ctcatctcta     120
accatgaaca gttgcccata ctgggcaacc gccctagaga gccagaaagg tgcagccgtg     180
gagctctgta                                                            190

<210> SEQ ID NO 78
<211> LENGTH: 148
<212> TYPE: DNA
<213> ORGANISM: Artificial Sequence
<220> FEATURE:
<223> OTHER INFORMATION: Description of Artificial Sequence: Reverse
      gene construct corresponding to a  specific region of
      the mouse Ii gene.

<400> SEQUENCE: 78
aacagcagca gcagcagcag cgcctgtggg aaaaactaga ggctagagcc atggatgacc      60
aacgcgacct catctctaac catgaacagt tgcccatact gggcaaccgc cctagagagc     120
cagaaaggtg cagccgtgga gctctgta                                        148

<210> SEQ ID NO 79
<211> LENGTH: 124
<212> TYPE: DNA
<213> ORGANISM: Artificial Sequence
<220> FEATURE:
<223> OTHER INFORMATION: Description of Artificial Sequence: Reverse
      gene construct corresponding to a  specific region of
      the mouse Ii gene.

<400> SEQUENCE: 79
tgtgggaaaa actagaggct agagccatgg atgaccaacg cgacctcatc tctaaccatg      60
aacagttgcc catactgggc aaccgcccta gagagccaga aggtgcagc cgtggagctc      120 tgta                                                                  124
```